US006506751B1

(12) United States Patent
Justus et al.

(10) Patent No.: US 6,506,751 B1
(45) Date of Patent: Jan. 14, 2003

(54) THIAZOLIDINONE COMPOUNDS USEFUL AS CHEMOKINE INHIBITORS

(75) Inventors: Stephanie Elizabeth Ault Justus, Livonia, MI (US); Helen Tsenwhei Lee, Ann Arbor, MI (US); Jason Keith Pontrello, Kalamazoo, MI (US); Bruce David Roth, Plymouth, MI (US); Karen Elaine Sexton, Ann Arbor, MI (US); Michael William Wilson, Ann Arbor, MI (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/705,219

(22) Filed: Nov. 2, 2000

Related U.S. Application Data

(60) Provisional application No. 60/165,395, filed on Nov. 12, 1999.

(51) Int. Cl.[7] .................... C07D 413/06; C07D 277/34; C07D 401/06; A61K 31/426; A61P 31/18

(52) U.S. Cl. .................... 514/236.8; 546/175; 546/187; 546/194; 546/209; 544/133; 548/182; 548/183; 548/186; 548/187; 514/314; 514/316; 514/326; 514/369

(58) Field of Search ........................ 544/133; 514/236.8, 514/369, 314, 316, 326; 548/182, 186, 187, 183; 546/175, 187, 194, 209

(56) References Cited

U.S. PATENT DOCUMENTS

| | | | | |
|---|---|---|---|---|
| 4,436,739 | A | 3/1984 | Krumkalns | 424/246 |
| 4,482,712 | A | 11/1984 | Krumkalns | 544/54 |
| 4,933,453 | A | 6/1990 | Hrib et al. | 544/297 |
| 4,992,455 | A | 2/1991 | Enomoto et al. | 514/342 |
| 5,037,984 | A | 8/1991 | Hrib et al. | 544/368 |
| 5,106,860 | A | 4/1992 | Enomoto et al. | 514/342 |
| 5,371,087 | A | 12/1994 | Hrib et al. | 514/252 |

FOREIGN PATENT DOCUMENTS

| | | |
|---|---|---|
| EP | 0010420 | 8/1984 |
| EP | 0091148 | 11/1987 |
| JP | 57085380 | 11/1980 |
| JP | 57088170 | 11/1980 |
| WO | 9605186 | 2/1996 |
| WO | 9620936 | 7/1996 |

OTHER PUBLICATIONS

Baggiolini et al., "Interleukin–8 and Related Chemotactic Cytokines—CXC and CC Chemokines", *Adv. Immunol.*, vol. 55, 1994, pp 97–179.

Oppenheim et al., "Properties of the novel proinflammatory supergene "intercrine" cytokine family", *Annu. Rev. Immunol.*, vol. 9, 1991, pp 617–648.

Murphy et al., "The Molecular Biology of Leukocyte Chemoattractant Receptors", *Annu. Rev. Immunol.*, vol. 12, 1994, pp 593–633.

Schall and Bacon, "Chemokines, Leukocyte trafficking, and inflammation", *Current Opinion in Immunology*, vol. 6, 1994, pp 865–873.

Gerard and Gerard, "The pro–inflammatory seven–transmembrane segment receptors of the leukocyte", *Current Opinion in Immunology*, vol. 6, 1994, pp 140–145.

Cocchi et al., "Identification of RANTES, MIP–1α and MIP–1βas the Major HIV–Suppressive Factors Produced by $CD8^+$ T Cells", *Science*, vol. 270, 1995, pp 1811–1815.

Feng et al., "HIV–1 Entry Cofactor: Functional cDNA Cloning of a Seven–Transmembrane, G Protein–Coupled Receptor", *Science*, vol. 272, 1996, pp 872–877.

Choe et al., "The β–Chemokine Receptors CCR3 and CCR5 Facilitate Infection by Primary HIV–1 Isolates", *Cell*, vol. 85, 1996, pp 1135–1148.

Alkhatib et al., "CC CKR5: A RANTES, MIP–1α MIP–1βReceptor as a Fusion Cofactor for Macrophage–Tropic HIV–1", *Science*, vol. 272, 1996, pp 1955–1958.

(List continued on next page.)

*Primary Examiner*—Mark L. Berch
*Assistant Examiner*—Kahsay Habte
(74) *Attorney, Agent, or Firm*—Lahive & Cockfield, LLP; Giulio A. DeConti, Jr.; Elizabeth A. Hanley

(57) ABSTRACT

Disclosed are compounds of the Formula I

I

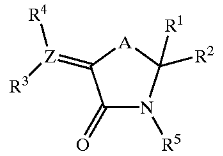

wherein:

Z is C or nothing, provided that when Z is nothing, $R^3$ and $R^4$ are nothing;

A is S, S═O or O═S═O;

$R^1$ and $R^2$ are independently hydrogen, lower alkyl, halogen, hydroxy or lower alkoxy, (un)substituted aryl, (un)substituted arylalkyl, (un)substituted heteroaryl or(un)substituted heteroarylakyl;

$R^3$ and $R^4$ independently represent hydrogen, lower alkyl, cycloalkyl, aminoalkyl, mono- or dialkylaminoalkyl, (un)substituted aryl or (un)substituted heteroaryl;

$R^5$ represents a (un)substituted carbocyclic group containing from 3–7 members, up to two of which members are optionally hetero atoms; or $R^5$ is $(CR^6R^7)—(CH_2)_n—XR^8R^9$;

X is S or N;

$R^6$, $R^7$, $R^8$, $R^9$, and n are as defined in the specification.

The compounds are useful in the treatment and prevention of the AIDS virus. Intermediates useful in the preparation of the final products, pharmaceutical compositions containing the final products are also taught.

28 Claims, No Drawings

OTHER PUBLICATIONS

Doranz et al., "A Dual–Tropic Primary HIV–1 Isolate That Uses Fusin and the β–Chemokine Receptors CKR–5, CKR–3, and CKR–2b as Fusion Cofactors", *Cell*, vol. 85, 1996, pp 1149–1158.

Deng et al., "Identification of a major co–receptor for primary isolates of HIV–1", *Nature*, vol. 381, 1996, pp 661–666.

Dragic et al., "HIV–1 entry into $CD4^+$ cells is mediated by the chemokine receptor CC–CKR–5", *Nature*, vol. 381, 1996, pp 667–673.

Liu et al., "Homozygous Defect in HIV–1 Coreceptor Accounts for Resistance of Some Multiply–Exposed Individuals to HIV–1 Infection", *Cell*, vol. 86, 1996, pp 367–377.

Samson et al., "Resistance to HIV–1 Infection in caucasian individuals bearing mutant alleles of the CCR–5 chemokine receptor gene", *Nature*, vol. 382, 1996, pp 722–725.

Dean et al., "Genetic Restriction of HIV–1 Infection and Progression to AIDS by a Deletion Allele of the CKR5 Structural Gene", *Science*, vol. 273, 1996, pp 1856–1862.

Huang et al., "The role of a mutant CCR5 allele in HIV–1 transmission and disease progression", *Nature Medicine*, vol. 2, No. 11, 1996, pp 1240–1243.

Miller and Krangel, "Biology and Biochemistry of the Chemokines: A Family of Chemotactic and Inflammatory Cytokines", *Critical Reviews in Immunology*, vol. 12(1,2), 1992, pp 17–46.

Sahu et al., "Studies on thiazolidinones. Part XIV: Synthesis of 3,3–bisthiazolidinones and 2,2–disubstituted thiazolidinones from azomethines", *J. Indian Chem. Soc.*, vol. 60, No. 9, 1983, pp 861–863.

THIAZOLIDINONE COMPOUNDS USEFUL AS CHEMOKINE INHIBITORS

This application claims the benefit of provisional application No. 60/165,395 filed Nov. 12, 1999.

BACKGROUND OF THE INVENTION

1. Field of the Invention

The present invention relates to certain thiazolidinone derivatives useful as modulators of the chemokine receptors, including CCR-1, CCR-2, CCR-2A, CCR-2B, CCR-3, CCR-4, CCR-5, CXCR-1, CXCR-2, CXCR-3, and/or CXCR-4 and to pharmaceutical compositions that include these compounds and a pharmaceutically acceptable carrier. In addition, the present invention is directed to methods for inhibiting HIV infectivity.

2. Summary of the Related Art

Chemokines mediate a range of proinflammatory effects on leukocytes, such as chemotaxis, degranulation, and intigran activation (Baggiolini et al., *Adv. Immunol.,* 1994;55:97–179; Oppenheim et al., *Annu. Rev. Immunol.,* 1991; 9:617–648; Miller et al., *Crit. Rev. Immunol.,* 1992;12:17–46). These effects are mediated by binding to the seven-transmembrane-spanning G-protein coupled receptors (Baggiolini et al.,*Adv. Immunol.,* 1994;55:97–179; Murphy, *Annu. Rev. Immunol.,* 1994;12:593–633; Schall et al., *Curr. Opin. Immunol.,* 1994;6:865–873; Gerard et al., *Curr. Opin. Immunol.,* 1994;6;140–145; Mackay, *Curr. Bio.,* In press). Chemokine receptors also serve as co-receptors for HIV-1 entry into cells. This came from observations that RANTES, MIP-1α, and MIP-1β suppressed infection of susceptible cells in vitro by macrophage-tropic primary HIV-1 isolates (Cocchi et al., *Science* (Wash. D.C.), 1995;270:1811–1815). The chemokine receptor CXCR-4 is found to support infection and cell fusion of $CD4^+$ cells by laboratory-adapted, T-tropic HIV-1 strains (Feng et al., *Science* (Wash. D.C.), 1996;272:872–877). CCR-5, a RANTES, MIP-1α, and MIP-1β receptor, is subsequently identified as the principle co-receptor for primary macrophage-tropic strains (Choe et al., *Cell,* 1996;85:1135–1148; Alkhatib et al., *Science* (Wash. D.C.), 1996;272:1955–1958; Doranz et al., *Cell,* 1996;85:1149–1158; Deng et al., *Nature* (Lond.) 1996;381:661–666; Dragic et al., *Nature* (Lond.), 1996;381:667–3). The importance of CCR-5 for HIV-1 transmission is underscored by the observation that certain individuals who had been repeatedly exposed to HIV-1 but remained uninfected had a defect in CCR-5 expression (Liu et al., *Cell,* 1996; 86:367–377; Samson et al., *Nature* (Lond.), 1996;382:722–725; Dean et al., *Science* (Wash. D.C.), 1996;273:1856–1862; Huang et al., *Nature Med.,* 1996;2:1240–1243). These noninfectable individuals are found to be homozygous for a defective CCR-5 allele that contains an internal 32-base pair deletion (CCR-5 Δ32). The truncated protein encoded by this gene is apparently not expressed at the cell surface. CCR-5 Δ32 homozygous individuals comprise ~1% of the Caucasian population and heterozygous individuals comprise ~20%. In studies of about 2700 HIV-1 infected individuals, no Δ32 homozygotes are found. Individuals who are heterozygous for Δ32 CCR-5 allele have been shown to progress more slowly to AIDS than wild-type homozygous individuals (Samson et al., *Nature* (Lond.), 1996;382:722–725; Dean et al., *Science* (Wash. D.C.), 1996;273:1856–1862; Huang et al., *Nature Med.,* 1996;2:1240–1243). Thus, the identity of CCR-5 as the principle co-receptor for primary HIV isolates provides an opportunity to understand disease pathogenesis, and more importantly to identify a new avenue for the treatment of HIV-1 infection.

The instant invention is a series of finctionalized heterocycles that block the CD-4/GP-120 interaction with CCR-5 receptor, and thus can be useful in the treatment of HIV infection manifested in AIDS.

SUMMARY OF THE INVENTION

The compounds of the invention are useful in a method of modulating chemokine receptor activity in a patient in need of such modulation, the method comprising the administration of an effective amount of the compound to a subject, preferably mammalian, in need thereof.

The present invention is directed to the use of thiazolidinone derivatives as modulators of chemokine receptor activity. In particular, these compounds are useful as modulators of chemokine receptors, including CCR-1, CCR-2, CCR-2A, CCR-2B, CCR-3, CCR-4, CCR-5, CXCR-3, CXCR1, CXCR2, and/or CXCR-4. In particular, the compounds of the present invention are preferred as modulators of the chemokine receptor CCR-5.

The compounds of the invention are those having the structure of Formula 1:

I

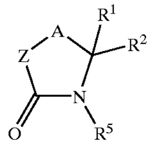

wherein:

Z is $-CH_2-$ or 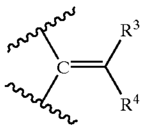 ;

A is S, S=O, or O=S=O;

$R^1$ and $R^2$ are independently hydrogen, lower alkyl, halogen, hydroxy, or lower alkoxy; or aryl, arylalkyl, heteroaryl, or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, sulfamoyl, or carbonylamino, provided $R^1$ and $R^2$ are not both hydroxy or lower alkoxy;

$R^3$ and $R^4$ independently represent hydrogen, lower alkyl, cycloalkyl, aminoalkyl, or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, sulfamoyl, or carbonylamino;

$R^5$ represents a carbocyclic group containing from 3–7 members, up to two of which members are optionally heteroatoms selected from oxygen and nitrogen, where the carbocyclic group is optionally substituted with one or two groups selected from halogen, lower alkyl, lower alkoxy, mono- or dialkylamino, aryl, arylalkyl, or a heterocyclic group; or $R^5$ is $(CR^6R^7)—(CH_2)_n—XR^8R^9$;

X is S or N;

$R^6$ and $R^7$ independently represent hydrogen, lower alkyl, hydroxy, amino, or mono- or dialkylamino;

n is 0, 1, 2, 3, or 4; and $R^8$ and $R^9$ independently represent hydrogen, lower alkyl, lower alkenyl, aminoalkyl, alkylaminoalkyl, dialkylaminoalkyl, or cycloalkyl; or $R^8$ and $R^9$ together with the nitrogen to which they are attached form a heterocyclic ring containing from 5–7 members, up to two of which members are optionally heteroatoms selected from oxygen, sulfur, and nitrogen, where the heterocyclic group is optionally substituted with one or two groups selected from halogen, lower alkyl, lower alkoxy, mono- or dialkylamino, aryl, heteroaryl, arylalkyl, heteroarylalkyl, cycloalkyl, or heterocyclic group.

Preferred compounds have Formula Ia

Ia

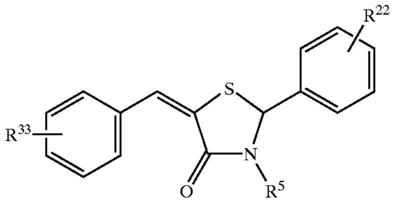

wherein $R^{22}$ and $R^{33}$ independently are hydrogen, halo, alkyl, and trihaloalkyl, and $R^5$ is as defined above. Especially preferred are such compounds wherein $R^5$ is alkyl such as propyl, substituted with a heterocyclic group such as piperidyl, piperazinyl, or morpholinyl, and where such heterocyclic group is unsubstituted or substituted with a cyclic or heterocyclic group such as cyclohexyl, pyridinyl, morpholino, piperidinyl, or pyrinidyl.

Another preferred set of compounds have Formula Ib

Ib

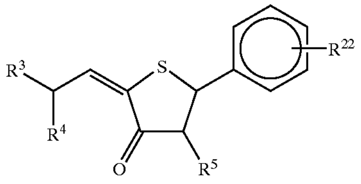

wherein $R^3$ and $R^4$ together form a heteroaryl ring such as pyridyl, pyrrolyl, and thienyl, $R^{22}$ is hydrogen, halo, alkyl, and haloalkyl, and $R^5$ is as defined above, and especially substituted alkyl.

The instant invention includes pharmaceutical compositions of compounds of Formula I and methods of using the compounds for modulating chemokine receptor activity, preventing or treating infection by HIV, delaying the onset of AIDS, treating AIDS, and treating inflammatory disease.

DETAILED DESCRIPTION OF THE INVENTION

The novel compounds encompassed by the instant invention are those described by the general Formula I set forth above, and the pharmaceutically acceptable salts, esters, amides, and prodrugs thereof.

Preferred compounds of Formula I are those in which $R^4$ is hydrogen; $R^3$ is dialkylaminoalkyl or aryl, heteroaryl, or cycloalkyl optionally substituted with halogen, lower alkyl, lower alkoxy, amino, or mono- or dialkylamino; A is S; and $R^1$ is hydrogen; $R^2$ is aryl or heteroaryl optionally substituted with halogen, lower alkyl, lower alkoxy, amino, or mono- or dialkylamino.

In addition to the compounds of Formula I, the invention encompasses compounds of Formula II:

II

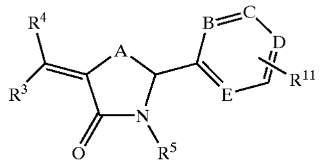

wherein $R^3$, $R^4$, $R^5$, and A are as defined above for Formula I;

$R^{11}$ is hydrogen, halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, sulfamoyl, or carbonylamino; and B, C, D, and E independently represent CH or N, provided that no more than two of B, C, D, and E are N.

Preferred compounds of Formula II are those in which all of B, C, D, and E are CH or only one of B, C, D, and E is nitrogen; $R^4$ is hydrogen; $R^3$ is dialkylaminoalkyl, or aryl, heteroaryl, or cycloalkyl, each of which is optionally substituted with halogen, lower alkyl, lower alkoxy, amino, or mono- or dialkylamino; and $R^{11}$ is hydrogen or halogen.

In addition, the invention encompasses compounds of Formula III:

III

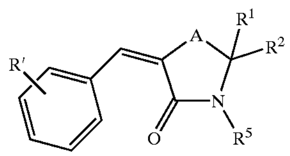

wherein $R^1$, $R^2$, $R^5$, and A are as defined above for Formula I and R' is as defined above for $R^{11}$ in Formula II.

Preferred compounds of Formula III are those in which $R^{11}$ is hydrogen; A is S; $R^2$ is dialkylaminoalkyl, or aryl, heteroaryl, or cycloalkyl, each of which is optionally substituted with halogen, lower alkyl, lower alkoxy, amino, or mono- or dialkylamino; and $R^{11}$ is hydrogen or halogen.

In addition, the invention encompasses compounds of Formula IV:

IV

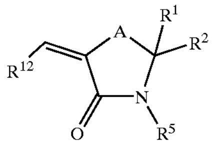

wherein $R^1$, $R^2$, $R^5$, and A are as defined above for Formula I; and $R^{12}$ is cycloalkyl or heteroaryl, each of which is optionally substituted with halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, sulfamoyl, or carbonylamino.

Preferred compounds of Formula IV are those in which $R^{12}$ is cyclohexyl, 2-, 3- or 4-pyridinyl, 2- or 3-thienyl, 2- or 3-furanyl, 2- or 3-pyrrolyl, or 2- or 3-quinolinyl, each of which is optionally substituted with halogen or lower alkyl; $R^1$ is hydrogen; A is S; and $R^2$ is dialkylaminoalkyl, or aryl, heteroaryl, or cycloalkyl, each of which is optionally substituted with halogen, lower alkyl, lower alkoxy, amino, or mono- or dialkylamino.

In addition, the invention encompasses compounds of Formula V:

V

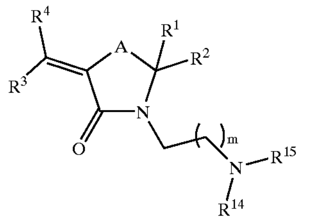

wherein

- $R^1$, $R^2$, $R^3$, $R^4$, and A are as defined above for Formula I;
- m is 0, 1, 2, or 3; and
- $R^{14}$ and $R^{15}$ independently represent hydrogen, lower alkyl, lower alkenyl, or cycloalkyl; or
- $R^{14}$ and $R^{15}$ together with the nitrogen to which they are attached form a heterocyclic ring containing from 5–7 members, up to two of which members are optionally heteroatoms selected from oxygen, sulfur, and nitrogen, where the heterocyclic group is optionally substituted with one or two groups selected from halogen, lower alkyl, lower alkoxy, mono- or dialkylamino, aryl, arylalkyl, or a heterocyclic group.

Preferred compounds of Formula V are those in which m is 2; and $R^{14}$ and $R^{15}$ independently represent hydrogen or lower alkyl, or $R^{14}$ and $R^{15}$ together with the nitrogen to which they are attached form a morpholine ring or a piperidine ring, each of which is optionally substituted with a heterocycle, aryl, or arylalkyl.

The terms "alkyl," "lower alkyl," or "($C_1$–$C_6$)-alkyl" mean a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents listed below for aryl.

The term "cycloalkyl" means a saturated hydrocarbon ring which contains from 3 to 7 carbon atoms, for example, cyclopropyl, cyclobutyl, cyclopentyl, cyclohexyl, adamantyl, and the like.

By "alkoxy," "lower alkoxy," or "($C_1$–$C_6$)-alkoxy" in the present invention is meant straight or branched chain alkoxy groups having 1 to 6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

The term "aryl" means an unsubstituted aromatic carbocyclic group having a single ring (eg, phenyl), multiple rings (eg, biphenyl), or multiple condensed rings in which at least one is aromatic (eg, 1,2,3,4-tetrahydronaphthyl, naphthyl, anthryl, or phenanthryl), unsubstituted or substituted by 1 to 3 substituents selected from alkyl, O-alkyl and S-alkyl, OH, SH, —CN, halogen, 1,3-dioxolanyl, $CF_3$, $NO_2$, $NH_2$, $NHCH_3$, $N(CH_3)_2$, NHCO-alkyl, $—(CH_2)_mCO_2H$, $—(CH_2)_mCO_2$-alkyl, $—(CH_2)_mSO_3H$, —NH alkyl, $—N(alkyl)_2$, $—(CH_2)_mPO_3H_2$, $—(CH_2)_mPO_3(alkyl)_2$, $—(CH_2)_mSO_2NH_2$, and $—(CH_2)_mSO_2NH$-alkyl wherein alkyl is defined as above and m is 0, 1, 2, or 3.

The term "aralkyl" or "arylalkyl" means an alkyl moiety (as defined above) substituted with an aryl moiety (also as defined above).

By halogen in the present invention is meant fluorine, bromine, chlorine, and iodine, and their monovalent radicals.

By heteroaryl (aromatic heterocycle) in the present invention is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, naphthyridinyl, benzimidazolyl, and benzoxazolyl. The term "substituted heterocycle" means a heterocycle substituted by 1 to 3 substituents selected from alkyl, O-alkyl and S-alkyl, OH, SH, —CN, halogen, 1,3-dioxolanyl, $CF_3$, $NO_2$, $NH_2$, $NHCH_3$, $N(CH_3)_2$, NHCO-alkyl, $—(CH_2)_mCO_2H$, $—(CH_2)_mCO_2$-alkyl, $—(CH_2)_mSO_3H$, —NH-alkyl, $—N(alkyl)_2$, $—(CH_2)_mPO_3H_2$, $—(CH_2)_mPO_3(alkyl)_2$, $—(CH_2)_mSO_2NH_2$, and $—(CH_2)_mSO_2NH$-alkyl wherein alkyl is defined as above and m is 0, 1, 2, or 3.

The term "heteroalkyl" means an alkyl moiety (as defined above) substituted with a heteroaryl moiety (also as defined above).

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *J. of Pharma. Sci.,* 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge supra., 1977).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

Representative compounds of the invention are shown below in Table 1, below. Each compound is assigned a number, which number will be referred to below in the working examples and in subsequent tables.

TABLE 1

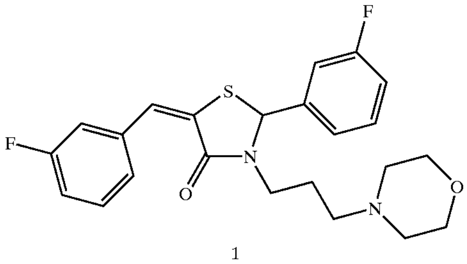

1

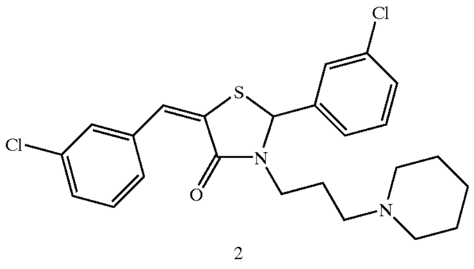

2

TABLE 1-continued

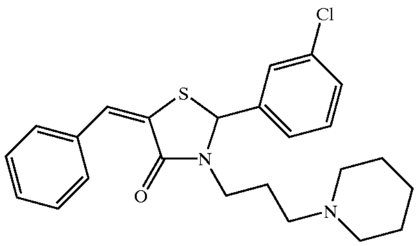

3

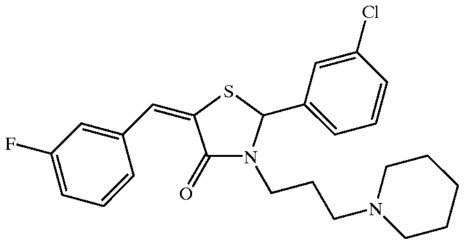

4

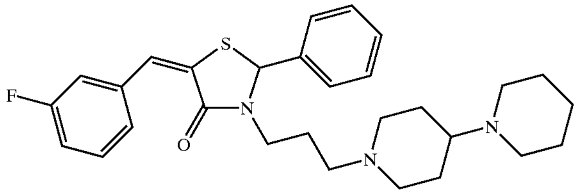

5

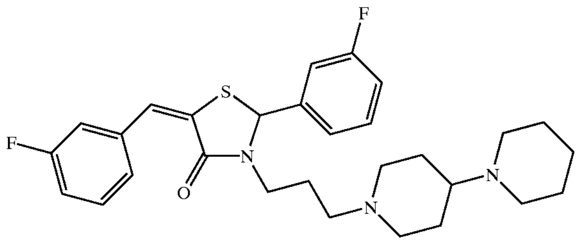

6

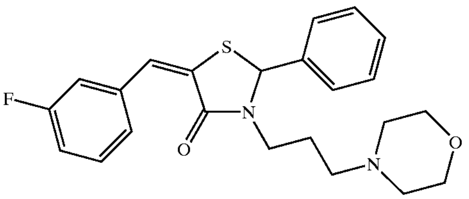

7

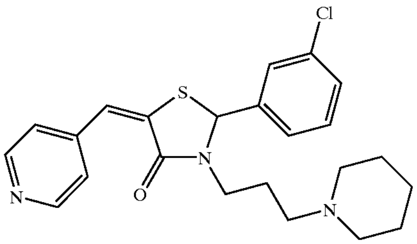

8

TABLE 1-continued
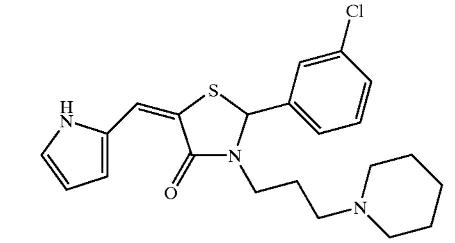
9
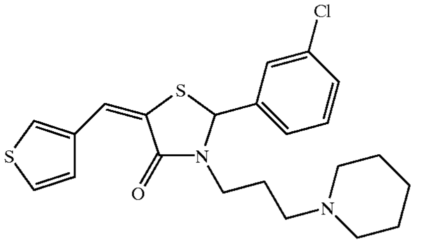
10
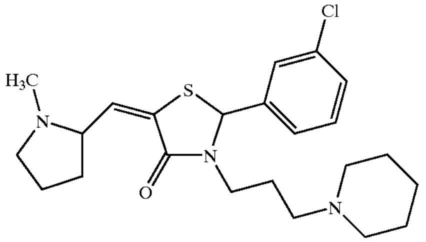
11
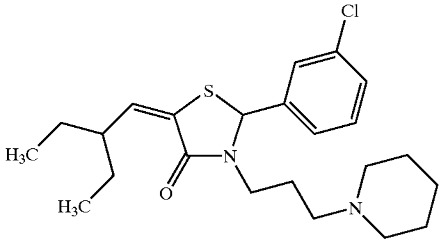
12
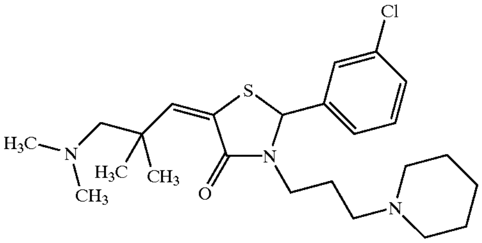
13
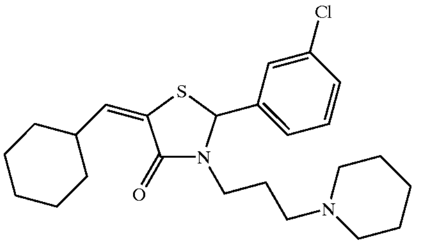
TABLE 1-continued
14
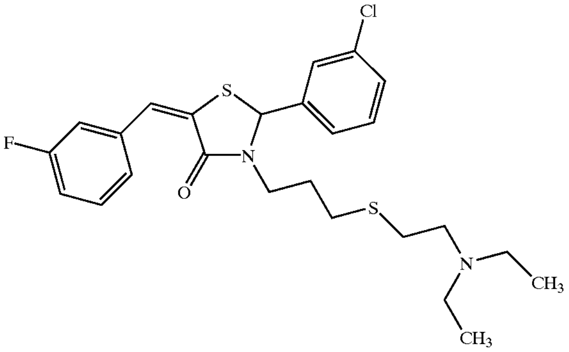
15
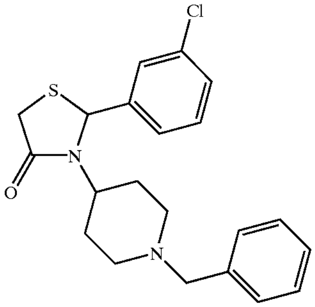
16
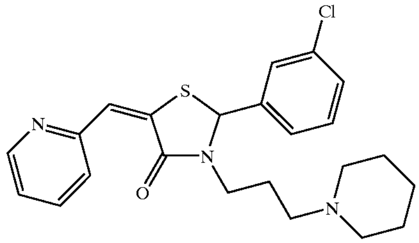
17
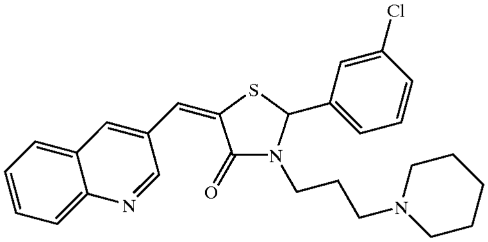
18
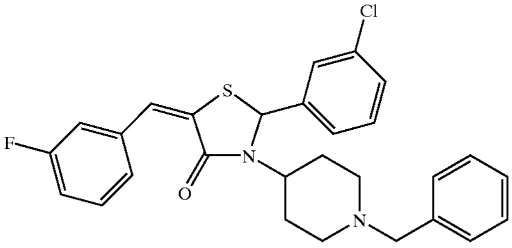
19

TABLE 1-continued

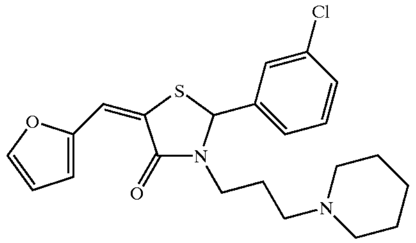

20

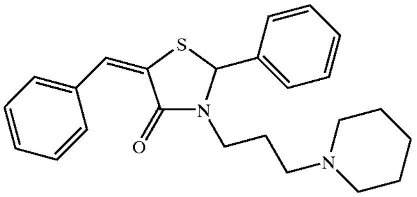

21

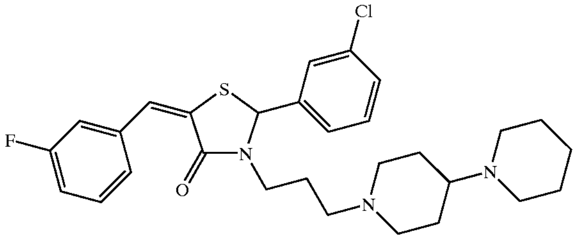

22

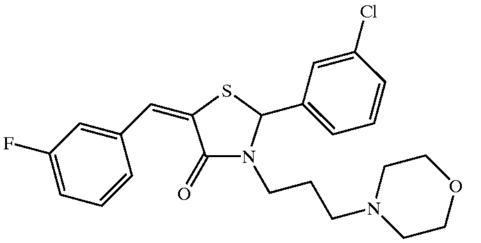

23

Representative compounds of the present invention, which are encompassed by Formula I include, but are not limited to, the compounds in Table 1 and their pharmaceutically acceptable acid or base addition salts, or amide or prodrugs thereof, as well as solvates and hydrates thereof.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula 1.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of HIV infection, the compounds utilized in the pharmaceutical method of this invention can be administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The compounds of Formula I are valuable antagonists of the CCR-5 chemokine receptor. As such, these compounds are useful scientific research tools for studying the role of CCR-5 in various biological processes in vitro. Compounds which are antagonists of the CCR-5 chemokine receptor are expected to have efficacy in inhibiting HIV infection and are thus useful in the treatment of AIDS. The compounds of the present invention are evaluated in a CCR-5 receptor binding assay (see below).

The examples presented below are intended to illustrate particular embodiments of the invention, and are not intended to limit the scope of the specification or the claims in any way.

An illustration of the preparation of compounds of the present invention is shown in Schemes 1–2. $R^1$, $R^{11}$, $R^8$, and $R^9$ are as defined above for Formula I.

Armed with the disclosure provided herein (particularly the schemes and the synthetic examples that follow) and knowledge common to all who practice in the field, those of ordinary skill in the art will be able to make and use the entire scope of compounds disclosed herein.

The invention compounds can be prepared by any of several synthetic methods, utilizing standard methodologies well-known to those skilled in organic chemistry. Preferred methods of synthesis of the final target compounds is shown in Schemes 1–2.

In Scheme 1, a Schiff base is first prepared from the corresponding aryl aldehyde and a haloalkylamine, for example, 3-chloropropylamine. The imine intermediate (Schiff base) is then reacted with a cyclizing agent such as mercaptoacetic acid to afford a substituted 4-thiazolidinone. The chloride is displaced with an amine in the presence of base, preferably a tertiary base, to afford the 3-aminosubstitutedpropyl-4-thiazolidinone. This thiazolidinone is reacted with an aryl aldehyde such as benzaldehyde in the presence of a strong base, as, for example, potassium t-butoxide, to yield the 5-methylene thiazolidinone of the invention.

Scheme 1

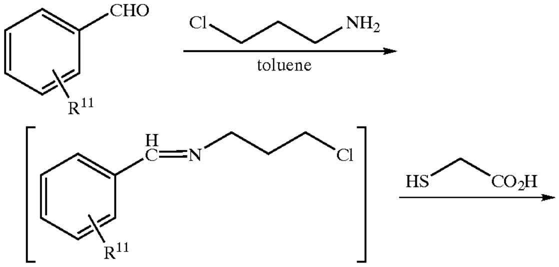

-continued

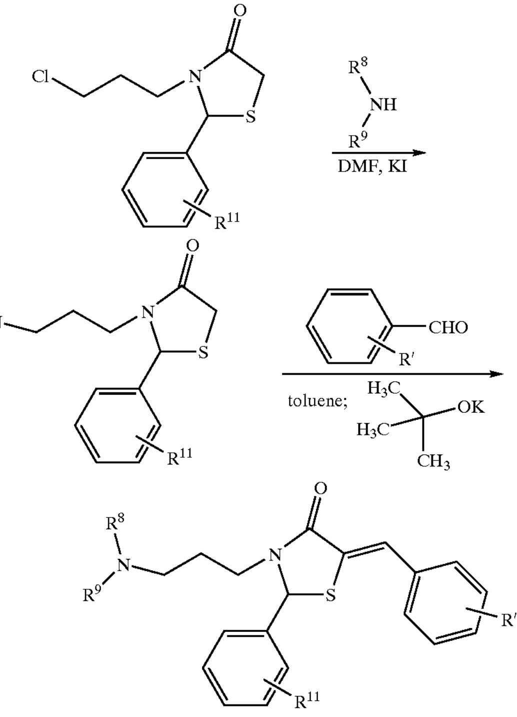

Alternatively, the synthetic sequence depicted in Scheme 2 can be used to prepare the compounds of the invention. For example, a benzaldehyde is reacted with a 3-aminosubstituted propylamine to afford a Schiff base. As in Scheme 1, the imine Schiff base intermediate is next reacted with mercaptoacetic acid at reflux to afford the corresponding 4-thiazolidinone. The 4-thiazolidinone is subsequently reacted with another benzaldehyde in the presence of a strong base, as, for example, potassium t-butoxide to yield the final product. The route shown in Scheme 2 is especially suited for preparing invention compounds having a second substituent at the 2-position of the 4-thiazolidinone.

Scheme 2

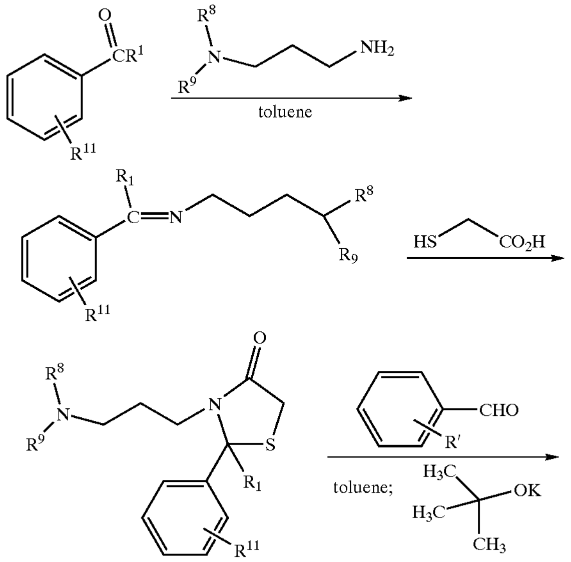

-continued

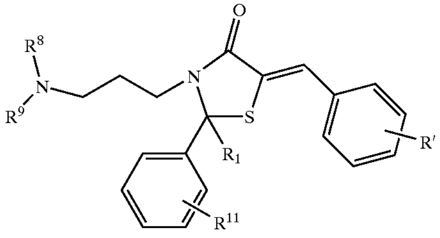

The present invention is further directed to combinations of the present compounds with one or more agents useful in the prevention or treatment of AIDS. For example, the compounds of this invention may be effectively administered, whether at periods of pre-exposure and/or postexposure, in combination with effective amounts of the anti-HIV compounds, immunomodulators, anti-infectives, or prophactic or therapeutic vaccines known to those of ordinary skill in the art. Examples of such compounds are found in Table 2, below.

TABLE 2

| Drug Name | Manufacturer | Indication |
|---|---|---|
| | ANTIVIRALS | |
| 097 | Hoechst/Bayer | HW infection, AIDS, ARC (non-nucleoside reverse transcriptase (RT) inhibitor) |
| GW141 W94/VX473 Amprenavir | Glaxo Wellcome | HIV infection, AIDS, ARC (protease inhibitor) |
| GW1592U89 Abacavir | Glaxo Wellcome | HW infection, AIDS, ARC (RT inhibitor) |
| Acemannan | Carrington Labs (Irving, Tx) | ARC |
| Acyclovir | Burroughs Wellcome | HIV infection, AIDS, ARC, in Combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination |
| Alferon Interferon | Inteferon Sciences | Kaposi's sarcoma, HIV in combination |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infections, AIDS, ARC |
| beta-fluoro-ddA | Nat'l Cancer Institute | AIDS-associated diseases |
| BMS-232623 (CGP-73547) | Bristol-Myers Squibb/Novartis | HIV infection, AIDS, ARC (protease inhibitor) |
| BMS-234475 (CGP-61755) | Bristol-Myers Squibb/Novartis | HIV infection, AIDS, ARC (protease inhibitor) |
| (-)6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Combivir AZT + 3TC | Glaxo Wellcome | HIV infection, AIDS, ARC |

TABLE 2-continued

| Drug Name | Manufacturer | Indication |
|---|---|---|
| Curdlan sulfate | AJI Pharma USA | HIV infection |
| Cytomegalovirus immune globin | MedImmune | CMV retinitis |
| Cytovene Ganciclovir | Syntex/Roche | Sight threatening CMV, peripheral CMV, retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| HIVID (ddc) Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | Triangle Pharmaceutical | HIV infection, AIDS, ARC (protease inhibitor) |
| Efavirenz (DMP 266) | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | Herpes zoster, herpes simplex |
| Foscavir/Foscarnet | Astra | CMV, HSV 1-2 |
| FTC | Triangle Pharmaceutical | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alpha-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| JE 2147 (KNI-764) (Protease inhibitor) | Japan Energy/ Agouron PI | HIV infection, AIDS, ARC (reverse transcriptase inhibitor); also with AZT |
| KNI-272 | Nat'l Cancer Institute | HIV-associated diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection - HBV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| PNU-140690 | Pharmacia Upjohn | HIV infection, AIDS, ARC (protease inhibitor) |
| Probucol | Vyrex | HIV infection, AIDS |
| RBD-CD4 | Sheffield Med. Tech (Houston, TX) | HIV infection, AIDS, ARC |
| Ritonavir | Abbott | HIV infection, AIDS, ARC (protease inhibitor) |
| S-1153 | Agouron/Shionogi | NnRTI |
| Saquinavir | Hoffmann-La Roche | HIV infection, AIDS, ARC (protease inhibitor) |
| Stavudine; d4T Didehydrodeoxy-thymidine | Bristol-Myers Squibb | HIV infection, AIDS, ARC |

TABLE 2-continued

| Drug Name | Manufacturer | Indication |
|---|---|---|
| Valaciclovir | Glaxo Wellcome | Genital HSV & CMV infections |
| Virazole Ribavirin | Viratek/ICN (Costa Mesa, CA) | Asymptomatic HIV positive, LAS, ARC |
| Zidovudine; AZT | Glaxo Wellcome | HIV infection, AIDS, ARC, Kaposi's sarcoma, in combination with other therapies |
| | IMMUNO-MODULATORS | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV core Particle Immunostimulant | Rorer | Seropositive HIV |
| IL-2 Interleukin-2 | Cetus | AIDS, in combination w/AZT |
| IL-2 Interleukin-2 | Hoffman-La roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-I | Imreg (New Orieans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK & F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| | ANTI-INFECTIVES | |
| Clindamycen with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Omidyl Eflomithine | Merrell Dow | PCP |
| Pentamidine Isethionate (IM & W) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | Cryptosporidial diarrhea |
| Intraconazole-R51211 | Janssen Pharm. | Histoplasmosis; cryptococcal meningitis |
| Trimetrexate | Warner-Lambert | PCP |
| | OTHER | |
| Daunorubicin | NeXstar, Sequus | Karposi's sarcoma |
| Recombinant Human Erythropoietin | Ortho Pharm. Corp. | Severe anemia associated with AZT therapy |
| Recombinant Human Growth Hormone | Serono | AIDS-related wasting, cachexia |
| Megestrol Acetate | Bristol-Myers Squibb | Treatment of anorexia associated w/AIDS |
| Testosterone | Alza, Smith Kline | AIDS-related wasting |
| Total Enteral Nutrition | Norwich Eaton Pharmaceuticals | Diarrhea and malabsorption related to AIDS |

The disclosures in this application of all articles and references, including patents, are incorporated herein by reference.

The invention is illustrated further by the following detailed examples. The examples are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLES

Example 1

Synthesis of 5-(3-Fluorobenzylidene)-2-(3-fluorophenyl)-3-(3-morpholin-4-ylpropyl)-thiazolidin-4-one (Compound I)

Step 1: 3-(3-Chloropropyl)-2-(3-fluorophenyl)-thiazolidin-4-one

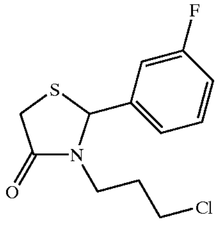

3-Fluorobenzaldehyde (1.58 mm, 17.7 mL), 3-chloropropylarnine (132 mm, 17.2 g), and diisopropylamine (132 mm, 23 mL) are mixed in 50 mL of toluene with a reflux condenser connected to a dean-stark trap. The imine intermediate is formed after 1 hour refluxing. Mercaptoacetic acid (211.2 mm, 14.7 mL) is then added to the mixture and the refluxing continued for another 17 hours. Toluene is evaporated, and the residue is re-dissolved in EtOAc (100 mL). The organic layer is washed with brine, dried and evaporated; the pure product is isolated by column chromatography (30% EtOAc/Hexane) to yield 30 g (74%).

Step 2: 2-(3-Fluorophenyl)-3-(3-morpholin-4-ylpropyl)-thiazolidin-4-one

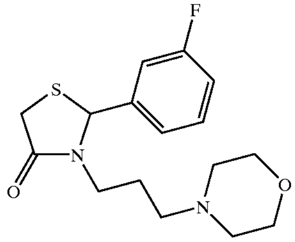

3-(3-Chloropropyl)-2-(3-fluorophenyl)-thiazolidin-4-one (1.15 mm, 0.315 g) and morpholine (1.15 mm, 0.1 g) are mixed in 20 mL DMF in the presence of N,N-diisopropylethylamine (1.15 mm, 0.2 mL) and a catalytic amount of KI. The mixture is heated at 60° C. for 24 hours, then 20 mL of EtOAc is added to the mixture. The organic layer is washed with brine and dried. The solvent is evaporated, and the residue is triturated with hexane, 0.31 g of the product is isolated (84%).

Step 3: 5-(3-Fluorobenzylidene)-2-(3-fluorophenyl)-3-(3-morpholin-4-ylpropyl)-thiazolidin-4-one 2-(3-Fluorophenyl)-3-(3-morpholin-4-ylpropyl)-thiazolidin-4-one (0.925 mm, 0.3 g) and 3-fluorobenzaldehyde (1.4 mm, 0.172 g) are mixed in 15 mL toluene followed by potassium t-butoxide (1.4 mm, 0.157 g). Molecular sieves are added, and the mixture is heated to 70° C. for 2 hours until the TLC showed the disappearance of starting material. The molecular sieves are removed by filtration. The solvent is evaporated, and the residue is dissolved in EtOAc, washed with brine, dried, and concentrated to dryness. Pure Compound 1 (0.3 g) is isolated by column chromatography (10% MeOH/$CH_2Cl_2$). MS: m/z (APCI, AP+) 431 $[M]^+$. MP 149–150° C.

Example 2

Synthesis of 5-(3-Chlorobenzylidene)-2-(3-chlorophenyl)-3-(3-piperidin-1-yl-propyl)-thiazolidin-4-one (Compound 2)

Step 1: 2-(3-Chlorophenyl)-3-(3-piperidin-1-yl-propyl)-thiazolidin-4-one

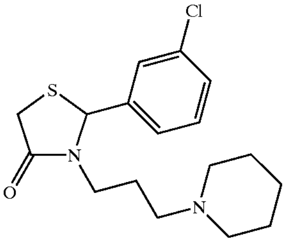

3-N-Piperidyl-propylamine (93 mm, 13.2 mL) is added to a solution of 3-chlorobenzaldehyde (115.2 mm, 13.1 mL) in toluene (50 mL). The mixture is heated under reflux for 2 hours. Mercaptoacetic acid (153.6 mm, 10.5 mL) is added to the reaction, and refluxing is continued for another 2 hours. The solvent is removed, and the crude product is used in the next step without further purification.

Step 2: 5-(3-Chlorobenzylidene)-2-(3-chlorophenyl)-3-(3-piperidin-1-yl-propyl)-thiazolidin-4-one 2-( 3-Chlorophenyl)-3-(3-piperidin-1-ylpropyl)-thiazolidin-4-one (3 mm, 1 g), 3-chlorobenzaldehyde (4.5 mm, 0.51 mL), and potassium t-butoxide (4.5 mm, 0.5 g) are mixed in 50 mL toluene with molecular sieves and heated at 60° C. for 4 hours. The molecular sieves are removed by filtration, and the solvent is concentrated to dryness. Pure Compound 2 (0.5 g) is isolated by column chromatography (5% MeOH/$CH_2Cl_2$). MS: m/z (APCI, AP+) 462 $[M]^+$. MP 137–139° C.

Example 3

The following compounds are prepared essentially according the procedures described in Examples 1–2 and shown in Schemes 1 and 2:

(a) 5-Benzylidene-2-(3-chlorophenyl)-3-(3-piperidin-1-yl-propyl)-thiazolidin-4-one (Compound 3) This compound is synthesized as Example 2, except that 3-chlorobenzaldehyde in Step 2 is replaced by benzaldehyde. MS: m/z (APCI, AP+) 427.0 $[M]^+$. $C_{24}H_{27}N_2OSCl.2.5\ H_2O$: Calcd: C, 61.13; H, 6.79; N, 5.94. Found C, 61.12; H, 6.31; N, 5.69.

(b) 2-(3-Chlorophenyl)-5-(3-fluorobenzylidene)-3-(3-piperidin-1-yl-propyl)-thiazolidin-4-one (Compound 4) This compound is synthesized as Example 2, except that 3-chlorobenzaldehyde in Step 2 is replaced by 3-fluorobenzaldehyde. MS: m/z (APCI, AP+) 445.0 $[M]^+$. $C_{24}H_{26}N_2OSFCl.1.5\ H_2O$: Calcd: C, 61.02; H, 6.18; N, 5.89. Found C, 61.29; H, 5.81; N, 5.78.

(c) 3-(3-[1,4']Bipiperidinyl-1'-yl-propyl)-5-(3-fluorobenzylidene)-2-phenyl-thiazolidin-4-one (Compound 5) This compound is synthesized as Example 1, except that 3-fluorobenzaldehyde in Step 1 is replaced by benzaldehyde, and morpholine is replaced by 4-piperidinopiperidine. MS: m/z (APCI, AP+) 494.2 $[M]^+$. $C_{29}H_{36}N_3OSF.1.33\ H_2O$: Calcd: C, 67.22; H, 7.47; N, 8.11. Found: C, 67.26; H, 7.19; N, 8.31.

(d) 3-(3-[1,4']Bipiperidinyl-1'-yl-propyl)-5-(3-fluorobenzylidene)-2-(3-fluorophenyl)-thiazolidin-4-one (Compound 6). This compound is synthesized as Example 1, except that morpholine is replaced by 4-piperidinopiperidine. MS: m/z (APCI, AP+) 512.2 $[M]^+$. MP 160–162° C.

(e) 5-(3-Fluorobenzylidene)-3-(3-morpholin-4-yl-propyl)-2-phenyl-thiazolidin-4-one (Compound 7). This compound is synthesized as Example 1, except that 3-fluorobenzaldehyde in Step 1 is replaced by benzaldehyde. MS: m/z (APCI, AP+) 413.2 $[M]^+$. $C_{23}H_{25}N_2O_2SF.0.5\ H_2O$: Calc'd: C, 65.48; H, 6.17; N, 6.64. Found: C, 65.19; H, 5.84; N, 6.43.

(f) 2-(3-Chlorophenyl)-3-(3-piperidin-1-yl-propyl)-5-(pyridin-4-yl-methylene)-thiazolidin-4-one (Compound 8). This compound is synthesized as Example 2, except that 3-chlorobenzaldehyde in Step 2 is replaced by 4-pyridinecarboxaldehyde. MS: m/z (APCI, AP+) 428.1 $[M]^+$. $C_{23}H_{26}N_3OSCl.H_2O$: Calcd: C, 61.88; H, 6.28; N, 9.42. Found: C, 61.57; H, 5.99; N, 8.78.

(g) 2-(3-Chlorophenyl)-3-(3-piperidin-1-yl-propyl)-5-(1H-pyrrol-2-yl-methylene)-thiazolidin-4-one (Compound 9). This compound is synthesized as Example 2, except that 3-chlorobenzaldehyde in Step 2 is replaced by 2-pyrrolecarboxaldehyde. MS: m/z (APCI, AP+) 416.1 $[M]^+$. $C_{22}H_{26}N_3OSCl.0.5\ H_2O$: Calcd: C, 62.12; H, 6.35; N, 9.88. Found: C, 61.87; H, 6.23; N, 9.72.

(h) 2-(3-Chlorophenyl)-3-(3-piperidin-1-yl-propyl)-5-(thiophen-3-yl-methylene)-thiazolidin-4-one (Compound 10). This compound is synthesized as Example 2, except that 3-chlorobenzaldehyde in Step 2 is replaced by 3-thiophenecarboxaldehyde. MS: m/z (APCI, AP+) 433.0 $[M]^+$. HPLC: 77.4%.

(i) 2-(3-Chlorophenyl)-5-(1-methyl-1H-pyrrol-2-ylmethylene)-3-(3-piperidin-1-yl-propyl)-thiazolidin-4-one (Compound 11). This compound is synthesized as Example 2, except that 3-chlorobenzaldehyde is replaced by N-methylpyrrolecarboxaldehyde. MS: m/z (APCI, AP+) 430.1 $[M]^+$.

(j) 2-(3-Chlorophenyl)-5-(2-ethylbutylidene)-3-(3-piperidin-1-yl-propyl)-thiazolidin-4-one (Compound 12). This compound is synthesized as Example 2, except that 3-chlorobenzaldehyde in Step 2 is replaced by 2-ethylbutyraldehyde. MS: m/z (APCI, AP+) 421.2 $[M]^+$.

(k) 2-(3-Chlorophenyl)-5-(3-dimethylamino-2,2-dimethylpropylidene)-3-(3-piperidin-1-yl-propyl)-thiazolidin-4-one (Compound 13). This compound is synthesized as Example 2, except that 3-chlorobenzaldehyde in Step 2 is replaced by 3-dimethylamino-2,2-dimethylpropionaldehyde. MS: m/z (APCI, AP+) 450.2 $[M]^+$. HPLC: 90.89%.

(l) 2-(3-Chlorophenyl)-5-cyclohexylmethylene-3-(3-piperidin-1-yl-propyl)-thiazolidin-4-one (Compound 14). This compound is synthesized as Example 2, except that 3-chlorobenzaldehyde in Step 2 is replaced by 3-cyclohexanebenzaldehyde. MS: m/z (APCI, AP+) 433.1 $[M]^+$. MP 90–91° C.

(m) 2-(3-Chlorophenyl)-3-[3-(2-diethylaminoethylsulfanyl)propyl]-5-(3-fluorobenzylidene)-thiazolidin-4-one (Compound 15). This compound is synthesized as Example 1, except that 3-fluorobenzaldehyde in Step 3 is replaced by 3-chlorobenzaldehyde and morpholine is replaced by 2-diethylaminoethanethiol. MS: m/z (APCI, AP+) 493.1 $[M]^+$. MP: 41–43° C.

(n) 3-(1-Benzylpiperidin-4-yl)-2-(3-chlorophenyl)-thiazolidin-4-one (Compound 16). This compound is synthesized as Example 2, Step 1, except that N-(3-aminopropyl)piperidine is replaced by N-benzyl-4-aminopiperidine. MS: m/z (APCI, AP+) 387.1 $[M]^+$. MP 140–141° C.

(o) 2-(3-Chlorophenyl)-3-(3-piperidin-1-yl-propyl)-5-(pyridin-3-ylmethylene)-thiazolidin-4-one (Compound 17). This compound is synthesized as Example 2, except that 3-chlorobenzaldehyde in Step 2 is replaced by 3-pyridinecarboxaldehyde. MS: m/z (APCI, AP+) 428.1 $[M]^+$. $C_{23}H_{26}N_3OSCl.0.67\ H_2O$: Calcd: C, 62.73; H, 6.21; N, 9.55. Found: C, 62.60; H, 5.97; N, 9.38.

(p) 2-(3-Chlorophenyl)-3-(3-piperidin-1-yl-propyl)-5-(quinolin-3-ylmethylene)-thiazolidin-4-one (Compound 18). This compound is synthesized as Example 2, except that 3-chlorobenzaldehyde in Step 2 is replaced by 3-quinolinecarboxaldehyde. MS: m/z (APCI, AP+) 478.1 $[M]^+$. $C_{27}H_{28}N_3SOCl.1.33\ H_2O$: Calcd: C, 64.53; H, 6.11; N, 8.37. Found: C, 64.88; H, 5.85; N, 8.15.

(q) 3-(1-Benzylpiperidin-4-yl)-2-(3-chlorophenyl)-5-(3-fluorobenzylidene)-thiazolidin-4-one (Compound 19). This compound is synthesized as Example 2, except that 3-chlorobenzaldehyde in Step 2 is replaced by 3-fluorobenzaldehyde and N-(3-aminopropyl) piperidine is replaced by N-benzyl-4-aminopiperidine. MS: m/z (APCI, AP+) 493.1 $[M]^+$. MP 121–123° C.

(r) 2-(3-Chlorophenyl)-5-(furan-2-ylmethylene)-3-(3-piperidin-1-yl-propyl)-thiazolidin-4-one (Compound 20). This compound is synthesized as Example 2, except that 3-chlorobenzaldehyde in Step 2 is replaced by 2-furancarboxaldehyde. MS: m/z (APCI, AP+) 417.1 $[M]^+$. MP 156–158° C.

(s) 3-(3-Azepan-1-ylpropyl)-5-benzylidene-2-phenyl-thiazolidin-4-one (Compound 21). This compound is synthesized as Example 2, except that N-(3-aminopropyl)piperidine is replaced by 3-hexamethyleneimino-1-propylamine. MS: m/z (APCI, AP+) 318 $[M]^+$. $C_{25}H_{30}N_2OS$. Calcd: C, 73.85; H, 7.44; N, 6.89. Found: C, 73.65; H, 7.43; N 6.75.

(t) 3-(3-[1,4']Bipiperidinyl-1'-yl-propyl)-2-(3-chlorophenyl)-5-(3-fluorobenzylidene)-thiazolidin-4-one (Compound 22). This compound is synthesized as in Example 1, except that 3-fluorobenzaldehyde in Step 1 is replaced by 3-chlorobenzaldehyde, and morpholine is replaced by 4-piperidinopiperidine. MS: m/z (APCI, AP+) 528 $[M]^+$. $C_{29}H_{35}ClFN_3OS.2HCl.3H_2O$: Calcd: C, 53.16; H, 6.63; N, 6.41. Found: C, 53.17; H, 6.79; N, 6.18.

(u) 2-(3-Chlorophenyl)-5-(3-fluorobenzylidene)-3-(3-morpholin-4-yl-propyl)-thiazolidin-4-one (Compound 23). This compound is synthesized as Example 1, except that 3-fluorobenzaldehyde is replaced by 3-chlorobenzaldehyde. $C_{23}H_{24}ClFN_2O_2S$. $C_{23}H_{24}N_2O_2SFCl$: Calcd: C, 61.81; H, 5.41; N, 6.27; Cl, 7.93; S, 7.17. Found: C, 61.60; H, 5.37; N, 6.11; Cl, 8.21; S, 7.38. MP 142–143° C.

(v) 5-Benzylidene-2-(3-chlorophenyl)-1-oxo-3-(3-piperidin-1-yl-propyl)-thiazolidin-4-one (Compound 24). 5-Benzylidene-2-(3-chlorophenyl)-3-(3-piperidin-1-yl-propyl)-thiazolidin-4-one (Compound 3) (0.10 g, 0.24 mmol) in 2 mL methanol is added to a solution of sodium periodate (0.13 g, 0.61 mmol) in 0.5 mL water. The reaction is stirred at ambient temperature for 2 days then partitioned between water and dichloromethane. The organic layer is dried ($MgSO_4$), concentrated and purified by column chromatography (5% $MeOH/CH_2Cl_2$) to give 78 mg of product in a 73% yield. MS: m/z (APCI, AP+) 443.1 $[M]^+$. $C_{24}H_{27}N_2SO_2Cl.1.33\ H_2O$: Calcd: C, 61.67; H, 6.07; N, 6.00. Found: C, 61.70; H, 5.97; N, 5.88.

Example 4

Combinatorial Solution Phase Synthesis

All reagents and solvents are obtained commercially and used without further purification or drying. Melting points are determined on a Thomas Hoover Unimelt melting point apparatus and are uncorrected. Analytical HPLC are performed on a Alltima C18 column (4.6 mm ID, 15 cm length), the mobile phase (acetonitrile/ water, 1.0 mL/min) with a linear gradient of 40% to 90% acetonitrile over 14 minutes. Detection is at 210 nm. Mass spectra are obtained on a Fison Instruments VG Platform II mass spectrometer using atmospheric pressure chemical ionization in both positive and negative switching modes. Proton NMR are recorded on a Varian Unity 400. The chemical shifts are reported in parts per million and the J values in hertz. Infrared spectra are recorded on a Matson FT-IR. Where indicated, reagents and solvents are dispensed by a Tecan RSP 5032 liquid handling robot. Solvents are removed by rotary evaporation or by a GeneVac HT12 Atlas Evaporator. Array reactions are conducted in either 16×125 mm screw top test tubes or 2 dram screw top vials, both stoppered with Teflon coated caps.

Reagent Pool

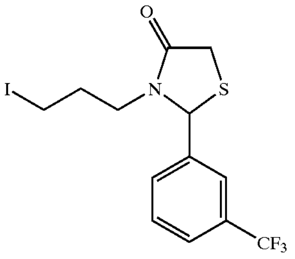

A

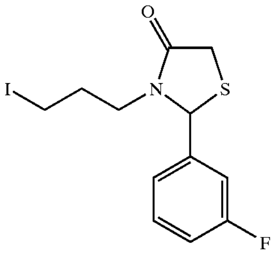

B

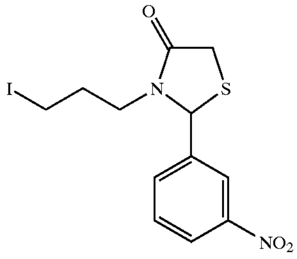

C

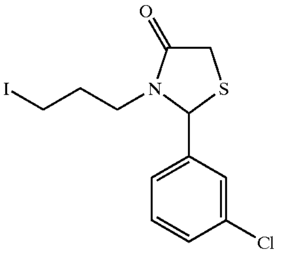

D

4-Thiazolidinone Reagent Pool

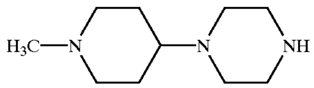

i

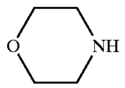

vi

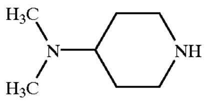

ii

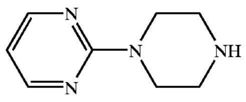

vii

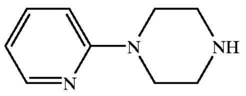

iii

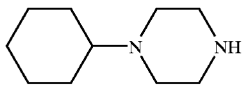

viii

-continued

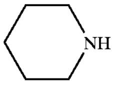

iv

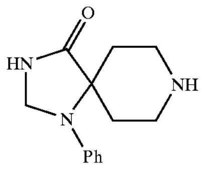

ix

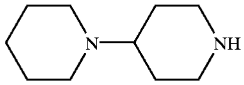

v

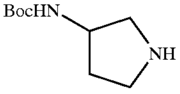

x

Amine Reagent Pool

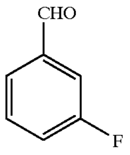

I

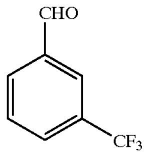

II

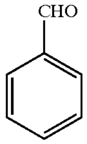

III

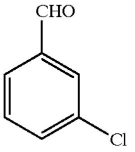

IV

Aldehyde Reagent Pool

Starting Material Preparation for Thiazolidinone-4-one Reagent Pool

The following compounds are prepared essentially according to the procedures described in Step 1, Examples 1 and 2.

1. 3-Chloropropyl Intermediates (a) 3-(3-choloropropyl)-2-(3-fluorophenyl)-thiazolidinone-4-one A mixture of 3-chlorobenzaldehyde (6.2 g, 44 mmol), mercaptoacetic acid (4.9 g, 54 mmol), 3-chloro-propylamine hydrochloride (2.9 g, 22 mmol) and diisopropylethyl amine (3.4 g, 26.4 mmol) in toluene (250 mL) are stirred and heated at reflux with azeotropic removal of water (Dean-Stark) for 3 hours. The solution is cooled and the solvent removed on a rotary evaporator. The residue is dissolved in EtOAc (200 mL) and the organic phase washed with a solution of saturated aqueous $NaHCO_3$ (3×). The organic phase is dried with $MgSO_4$, filtered, and concentrated. The residue is purified by flash chromatography on silica gel (EtOAc/hexane eluent) to give 5.5 g (91%) of desired 3-(3-choloropropyl)-2-(3-fluorophenyl)-thiazolidinone-4-one. $^1H$ NMR (400 MHz, $CDCl_3$) δ: 1.82–1.93 (1 H, m), 1.97–2.07 (1 H, m), 2.89–2.97 (1 H, m), 3.47–3.54 (2 H, m), 3.67–3.84 (5 H, m), 5.61 (1 H, d, J=1.7 Hz), 7.00–7.10 (3 H, m), 7.34–7.39 (1 H, m). $C_{12}H_{13}ClFNOS.0.5H_2O$. Calcd: C, 50.97; H, 4.99; N, 4.95. Found: C, 50.62; H, 4.60; N, 4.64. MS: m/z (APCI, AP+) 273 $[M]^+$.

(b) 3-(3-choloropropyl)-2-(3-chlorophenyl)-thiazolidinone-4-one

Obtained 4.9 g (77%). $^1H$ NMR (400 MHz, $CDCl_3$) δ: 1.80–1.91(1 H, m), 1.95–2.05 (1 H, m), 2.86–2.93 (1 H, m), 3.46–3.49 (2 H, m), 3.65–3.82 (5 H, m), 5.57 (1 H, d, J=1.2 Hz), 7.16–7.32 (4 H, m). $C_{12}H_{13}Cl_2NOS$. Calcd: C, 49.66; H, 4.52; N, 4.83; Cl, 24.43. Found: C, 49.60; H, 4.34; N, 4.71; Cl, 24.39. MS: m/z (APCI, AP+) 291 $[M+H]^+$.

(c) 3-(3-Choloropropyl)-2-(3-nitrophenyl)-thiazolidinone-4-one

Obtained 4.8 g (73%). $^1H$ NMR (400 MHz, $CDCl_3$) 67 : 1.81–1.91 (1 H, m), 1.98–2.08 (1 H, m), 2.86–2.93 (1 H, m), 3.46–3.52 (2 H, m), 3.65–3.86 (3 H, m), 5.71 (1 H, d, J=1.5 Hz), 7.57–7.65 (2 H, m), 8.17–8.23 (2 H, m). $C_{12}H_{13}ClN_2O_3S$. Calcd: C, 47.92; H, 4.36; N, 9.31. Found: C, 47.93; H, 4.60; N, 8.97. MS: m/z (APCI, AP+) 301 $[M+H]^+$.

(d) 3-(3-Choloropropyl)-2-(3-trifluromethylphenyl)-thiazolidinone-4-one

Obtained 5.5 g (77%). $^1H$ NMR (400 MHz, $CDCl_3$) 67 : 1.77–1.92 (1 H, m), 1.93–2.01 (1 H, m), 2.80–2.87 (1 H, m), 3.41–3.45 (2 H, m), 3.62–3.80 (3 H, m), 5.62 (1 H, d, J=1.9 Hz), 7.44–7.59 (4 H, m). $C_{13}H_{13}ClF_3NOS$. Calcd: C, 48.23; H, 4.04; N, 4.33; S, 9.90. Found: C, 48.11; H, 3.99; N, 4.34; S, 9.95. MS: m/z (APCI, AP+) 324 $[M+H]^+$.

2. 3-Iodopropyl Intermediates (a) 3-(3-Iodopropyl)-2-(3-flurophenyl)-thiazolidinone-4-one A solution of 3-(3-choloropropyl)-2-(3-chlorophenyl)-thiazolidinone-4-one (4.8 g, 16.5 mmol) in 2-propanone (200 mL) is treated with NaI (3.8 g, 25.5 mmol) and then heated to reflux for 16 hours. The solution is cooled and the solid filtered. The supernate is concentrated and filtered through a plug of flash silica gel (EtOAc eluent) to provide 5.8 g (92%) of 3-(3-iodopropyl)-2-(3-chlorophenyl)-thiazolidinone-4-one. $^{1}H$ NMR (400 MHz, $CDCl_3$) δ: 1.85–1.98 (1 H, m), 2.0–2.12 (1 H, m), 2.79–2.86 (1 H, m), 3.02–3.12 (2 H, m), 3.60–3.82 (3 H, m), 5.58 (1 H, d, J=1.7 Hz), 6.97–7.23 (3 H, m), 7.27–7.49 (1 H, m). $C_{12}H_{13}FINOS$. Calcd: C, 39.47; H, 3.84; 8.78; S, 8.78. Found: C, 39.69; H, 3.35; N, 3.66; S, 9.11. MS: m/z (APCI, AP+) 365[M]$^+$.

(b) 3-(3-Iodopropyl)-2-(3-chlorophenyl)-thiazolidinone-4-one $^{1}H$ NMR (400 MHz, $CDCl_3$) δ: 1.85–1.94 (1 H, m), 1.96–2.09 (1 H, m), 2.78–2.85 (1 H, m), 3.02–3.11 (2 H, m), 3.61–3.82 (3 H, m), 5.56 (1 H, d, J=1.9 Hz), 7.16–7.34 (4 H, m). $C_{12}H_{13}ClINOS$. Calcd: C, 37.76; H, 3.43; N; 3.67. Found: C, 38.15; H, 3.27; 3.58. MS: m/z (APCI, AP+) 382 [M+H]$^+$.

(c) 3-(3-iOdopropyl)-2-(3-nitrophenyl)-thiazolidinone-4-one $^{1}H$ NMR (400 MHz, $CDCl_3$) δ: 1.73–1.89 (1 H, m), 1.91–2.07 (1 H, m), 2.74–2.98 (1 H, m), 3.00–3.07 (2 H, m), 3.59–3.82 (3 H, m), 5.67 (1 H, d, J=1.7 Hz), 7.54–7.63 (2 H, m), 8.14–8.20 (2 H, m). $C_{12}H_{13}IN_2O_3S$. Calcd: C, 36.75; H, 3.34; N, 7.14. Found: C, 37.08; H, 3.47; N, 6.82. MS: m/z (APCI, AP+) 392 [M+H]$^+$.

(d) 3-(3-iodoPropyl)-2-(3-trifluromethylphenyl)-thiazolidinone-4-one $^{1}H$ NMR (400 MHz, $CDCl_3$) δ: 1.79–1.90 (1 H, m), 1.95–2.05 (1 H, m), 2.73–2.87 (1 H, m), 2.97–3.06 (2 H, m), 3.56–3.80 (3 H, m), 5.61 (1 H, d, J=1.7 Hz), 7.28–7.59 (4 H, m). $C_{13}H_{13}F_3INOS$. Calcd: C, 37.61; H, 3.16; N, 3.37; S, 7.72. Found: C, 37.87; H, 2.85; N, 3.16; S, 8.08. MS: m/z (APCI, AP+) 416 [M+H]$^+$.

Combinatorial Synthesis

The four respective 3-(3-iodopropyl)-2-(3-substituted-phenyl)-thiazolidinone-4-ones are dissolved in DMF and brought to a concentration of 0.5 M (25 mL total). The ten respective amines are dissolved in DMF and brought to a concentration of 0.3 M (25 mL total). A 0.5 M solution of diisopropylethyl amine (150 mL total) in DMF is made. Using the Tecan liquid handling robot, 3-(3-iodopropyl)-2-(3-trifluromethylphenyl)-thiazolidinone4-one (2.5 mL of 0.5 M solution, 1.26 mmol) is added to each well in column A (Array diagram shown in Table 3, below). In a likewise fashion solutions of 3-(3-iodopropyl)-2-(3-flurophenyl)-thiazolidin-4-one, 3-(3-iodopropyl)-2-(3-nitrophenyl)-thiazolidin-4-one and 3-(3-iodopropyl)-2-(3-chlorophenyl)-thiazolidin-4-one are added to wells in columns B, C, and D, respectively.

TABLE 3

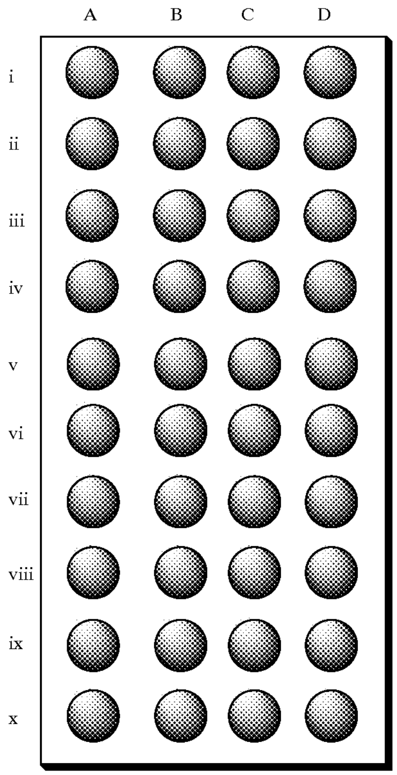

Array Format

Using the Tecan liquid handling robot 1-(4-(1-methyl-piperidinyl))-piperazine (i) (4 mL of a 0.3 M solution, 1.2 mmol) is dispensed to each well in row i. Likewise, solutions of, 4-N,N-dimethylamino-piperidine (ii), 1-(2-pyridyl) piperazine (iii), piperidine (iv), 4-piperidino-piperidine (v), morpholine (vi), 1-(2-pyrimidyl)piperazine (vii), 1-cyclohexylpiperazine (viii), phenyl-1,3,8-triazaspiro-[4,5] decan-4-one (ix), and 3-(tert-butoxycarbonylamino) pyrrolidine (x) are added to rows ii, iii, iv, v, vi, vii, viii, ix, and x, respectively. Diisopropylethyl amine (2.64 mL of a 0.5 M solution, 1.32 mmol) is then added to every well via the liquid handling robot. The 40 vessels are capped and heated overnight at 73 C. with agitation. The solutions are cooled and treated with polystyrene supported isocyanate resin (0.3 g, 1.7 mmol/g, 0.5 mmol). The heterogeneous mixtures are agitated 4 hours at room temperature and concentrated with the GeneVac. The contents of each vial is dissolved in $CHCl_3$ and placed on top of a Varian Chem Elut “hydromatrix” column (CE1003) which has been pre-washed with 2 M HCl. The product is eluted from each column with $CHCl_3$ (5 mL). The eluents are treated with $MgSO_4$, filtered, and concentrated into 2 dram pre-weighed vials with a GeneVac solvent concentrator.

The individual samples are dissolved in methanol (4.5 mL) and split into four new plates by the transfer of 1 mL aliquots. This creates four identical 4×10 arrays.

Array 1 is diluted with toluene (2 mL), and each well is treated with 3-fluorobenzaldehyde (I) (2 mL of a 0.3 M solution, 0.6 mmol), followed by the addition of 3 Å molecular sieves (~10 pellets). Potassium tert-butoxide (0.9 mL of a 1 M solution in THF, 0.9 mmol) is then added, and the mixtures are heated to 65° C. for 5 hours, cooled to room temperature, and treated with polyamine resin (0.2 g) (Booth and Hodges, *J. Am. Chem. Soc.,* 1997; 119:4882) and basic alumina (activity grade I, 0.3 g), and agitated overnight at room temperature. Each individual reaction is placed on top of an acidic ion exchange column (Baker 7090–07) previously treated with a water/methanol solution. The columns are eluted with methanol (5 mL) to remove impurities followed by ammonia in methanol (5 mL of a 2 M solution, 10 mmol) to elute the products. The individual methanolic ammonia fractions are placed into pre-weighed 2 dram vials and concentrated on the GeneVac.

In a likewise fashion array 2 is reacted with 3-trifluoromethyl-benzaldehyde (II), array 3 with benzaldehyde (III), and array 4 with 3-chlorobenzaldehyde (IV). The products are purified in the manner of array 1.

Results of Array Synthesis

Results of the combinatorial synthesis of new Thiazolidinone compounds are shown in Table 4, below.

TABLE 4

| Cmpd # | IUPAC Name | Reagent 1 (Thiazolidin-4-one) | Reagent 2 (amine) | Reagent 3 (aldehyde) | LC-MS | HPLC RT (min) |
|---|---|---|---|---|---|---|
| 25 | 5-(3-Fluoro-benzylidene)-3-(3-piperidin-1-yl-propyl)-2-(3-trifluoromethyl-phenyl)-thiazolidin-4-one | A | 4 | I | 479 | 3.0 |
| 26 | 5-(3-Fluoro-benzylidene)-2-(3-fluoro-phenyl)-3-[3-(4-pyridin-2-yl-piperazin-1-yl)-propyl]-thiazolidin-4-one | B | 3 | I | 507 | 2.3 |
| 27 | 3-[3-(4-Cyclohexyl-piperazin-1-yl)-propyl]-5-(3-fluoro-benzylidene)-2-(3-fluoro-phenyl)-thiazolidin-4-one | B | 8 | I | 512 | 2.5 |
| 28 | 2-(3-Chloro-phenyl)-5-(3-fluoro-benzylidene)-3-[3-(4-pyridin-2-yl-piperazin-1-yl)-propy1]-thiazolidin-4-one | D | 3 | I | 523 | 2.4 |
| 29 | 2-(3-Chloro-phenyl)-5-(3-fluoro-benzylidene)-3-[3-(4-pyrimidin-2-yl-piperazin-1-yl)-propyl]-thiazolidin-4-one | D | 7 | I | 524 | 3.0 |
| 30 | 2-(3-Chloro-phenyl)-3-[3-(4-pyridin-2-yl-piperazin-1-yl)-propyl]-5-(3-trifluoromethyl-benzylidene)-thiazolidin-4-one | D | 3 | II | 573 | 2.7 |
| 31 | 2-(3-Chloro-phenyl)-3-(3-piperidin-1-yl-propyl)-5-(3-trifluoromethyl-benzylidene)-thiazolidin-4-one | D | 4 | II | 495 | 3.3 |
| 32 | 2-(3-Chloro-phenyl)-3-[3-4-pyrimidin-2-yl-piperazin-1-yl)-propyl]-5-(3-trifluoromethyl-benzylidene)-thiazolidin-4-one | D | 7 | II | 574 | 3.3 |
| 33 | 5-Benzylidene-3-[3-(4-pyridin-2-yl-piperazin-1-yl)-propyl]-2-(3-trifluoromethyl-phenyl)-thiazolidin-4-one | A | 3 | III | 539 | 2.4 |
| 34 | 5-Benzylidene-3-[3-(4-pyrimidin-2-yl-piperazin-1-yl)-propyl]-2-(3-trifluoromethyl-phenyl)-thiazolidin-4-one | A | 7 | III | 540 | 3.0 |
| 35 | 5-Benzylidene-2-(3-fluoro-phenyl)-3-[3-(4-pyridin-2-yl-piperazin-1-yl)-propyl]-thiazolidin-4-one | B | 3 | III | 489 | 2.2 |
| 36 | 5-Benzylidene-2-(3-fluoro-phenyl)-3-(3-piperidin-1-yl-propyl)-thiazolidin-4-one | B | 4 | III | 411 | 2.8 |
| 37 | 5-Benzylidene-3-(3-[1,4']bipiperidinyl-1'-yl-propyl)-2-(3-fluoro-phenyl)-thiazolidin-4-one | B | 5 | III | 494 | 2.1 |
| 38 | 5-Benzylidene-3-[3-(4-cyclohexyl-piperazin-1-yl)-propyl]-2-(3-fluoro-phenyl)-thiazolidin-4-one | B | 8 | III | 494 | 2.4 |
| 39 | 5-Benzylidene-2-3-nitro-phenyl)-3-[3-(4-pyrimidin-2-yl-piperazin-1-yl)-propyl]-thiazolidin-4-one | C | 7 | III | 517 | 5.2 |

TABLE 4-continued

| Cmpd # | IUPAC Name | Reagent 1 (Thiazolidin-4-one) | Reagent 2 (amine) | Reagent 3 (aldehyde) | LC-MS | HPLC RT (min) |
|---|---|---|---|---|---|---|
| 40 | 5-Benzylidene-2-(3-chloro-phenyl)-3-[3-(4-pyridin-2-yl-piperazin-1-yl)-propyl]-thiazolidin-4-one | D | 3 | III | 505 | 2.4 |
| 41 | 5-Benzylidene-3-(3-[1,4']bipiperidinyl-1'-yl-propyl)-2-(3-chloro-phenyl)-thiazolidin-4-one | D | 5 | III | 510 | 2.3 |
| 42 | 5-Benzylidene-2-(3-chloro-phenyl)-3-(3-morpholin-4-yl-propyl)-thiazolidin-4-one | D | 6 | III | 429 | 2.7 |
| 43 | 5-Benzylidene-2-(3-chloro-phenyl)-3-[3-(4-pyrimidin-2-yl-piperazin-1-yl)-propyl]-thiazolidin-4-one | D | 7 | III | 506 | 2.9 |
| 44 | 5-Benzylidene-2-(3-chloro-phenyl)-3-[3-(4-cyclohexyl-piperazin-1-yl)-propyl]-thiazolidin-4-one | D | 8 | III | 510 | 2.6 |
| 45 | 5-(3-Chloro-benzylidene)-3-[3-(4-pyrimidin-2-yl-piperazin-1-yl)-propyl]-2-(3-trifluoromethyl-phenyl)-thiazolidin-4-one | A | 7 | IV | 574 | 3.3 |
| 46 | 5-(3-Chloro-benzylidene)-3-[3-(4-cyclohexyl-piperazin-1-yl)-propyl]-2-(3-rifluoromethyl-phenyl)-thiazolidin-4-one | A | 8 | IV | 578 | 2.9 |
| 47 | 5-(3-Chloro-benzylidene)-2-(3-fluoro-phenyl)-3-[3-(4-pyridin-2-yl-piperazin-1-yl)-propyl]-thiazolidin-4-ne | B | 3 | IV | 523 | 2.5 |
| 48 | 5-(3-Chloro-benzylidene)-2-(3-fluoro-phenyl)-3-[3-(4-pyrimidin-2-yl-piperazin-1-yl)-propyl]-thiazolidin-4-one | B | 7 | IV | 524 | 3.0 |
| 49 | 5-(3-Chloro-henzylidene)-3-[3-(4-cyclohexyl-piperazin-1-yl)-propyl]-2-(3-fluoro-phenyl)-thiazolidin-4-one | B | 8 | IV | 528 | 2.7 |
| 50 | 5-(3-Chloro-benzylidene)-2-(3-chloro-phenyl)-3-[3-(4-pyridin-2-yl-piperazin-1-yl)-propyl]-thiazolidin-4-one | D | 3 | IV | 539 | 2.6 |
| 51 | 5-(3-Chloro-benzylidene)-2-(3-chloro-phenyl)-3-[3-(4-pyrimidin-2-yl-piperazin-1-yl)-propyl]-thiazolidin-4-one | D | 7 | IV | 540 | 3.2 |
| 52 | 5-(3-Chloro-benzylidene)-2-(3-chloro-phenyl)-3-[3-(4-cyclohexyl-piperazin-1-yl)-propyl]-thiazolidin-4-one | D | 8 | IV | 544 | 2.8 |

Example 5

CCR-5 Receptor Binding Assay

The $^{125}$I-gp120/sCD4/CCR-5 binding assay is carried out similarly as described in Wu et al., *Nature,* 1996;384:179–183. Briefly, the envelope gp120 protein derived from HIV-1 JR-FL (Trkola et al., *Nature,* 1996;384:184–186), a M-tropic strain, is iodinated using solid phase lactoperoxidase to a specific activity of 20 $\mu$Ci/$\mu$g. For each binding reaction (in a final volume of 100 $\mu$L binding buffer [50 mM HEPES, pH 7.5, 1 mM $CaCl_2$, 5 mM $MgCl_2$, and 0.5% BSA]), 25 $\mu$L (2.5 $\mu$g) of membranes prepared from CCR-5/L 1.2 cells are mixed with 25 $\mu$L (3 nM) sCD4, followed by 25 $\mu$L (0.1 nM) radiolabeled gp120 in the presence or absence of 25 $\mu$L compound dissolved in DMSO (final concentration of DMSO 0.5%). The reactions are incubated at room temperature for 45 to 60 minutes and stopped by transferring the mixture to GFB filter plates, which are then washed 3 to 4 times with binding buffer containing 0.5 M NaCl. The plates are dried and MicroScint scintillation fluid is added before counting.

The results of the CCR-5 assay are shown in Table 5, below. For Compounds 1–24, results of the assay are expressed as $IC_{50}$ ($\mu$M), while for Compounds 25–52, results are expressed as % Inhibition at 10 $\mu$M. As seen in Table 5, the compounds of the invention, represented by Formula I, block the sCD-4/GP-120 binding to CCR-5 receptor with affinity less than or equal to 20 $\mu$M.

TABLE 5

| Compound # | $IC_{50}$ (μM) |
|---|---|
| 1 | 10.8 |
| 2 | 0.25 |
| 3 | 0.28 |
| 4 | 0.20 |
| 5 | 0.71 |
| 6 | 1.26 |
| 7 | 0.14 |
| 8 | 0.78 |
| 9 | 0.39 |
| 10 | 1.04 |
| 11 | 0.98 |
| 12 | 6.64 |
| 13 | 2.82 |
| 14 | 0.46 |
| 15 | 12.67 |
| 16 | 3.81 |
| 17 | 0.071 |
| 18 | 4.12 |
| 19 | 0.28 |
| 20 | 0.17 |
| 21 | 1.4 |
| 22 | 0.4 |
| 23 | 1.99 |
| 24 | 3.10 |
| | %Inhib. @ 10 μM |
| 25 | 50.7 |
| 26 | 75.3 |
| 27 | 57.6 |
| 28 | 78.8 |
| 29 | 86.8 |
| 30 | 61.7 |
| 31 | 54.4 |
| 32 | 81.8 |
| 33 | 62.0 |
| 34 | 79.2 |
| 35 | 76.2 |
| 36 | 63.3 |
| 37 | 56.6 |
| 38 | 54.4 |
| 39 | 70.1 |
| 40 | 84.3 |
| 41 | 62.4 |
| 42 | 64.7 |
| 43 | 95.0 |
| 44 | 54.5 |
| 45 | 57.7 |
| 46 | 51.1 |
| 47 | 75.6 |
| 48 | 84.7 |
| 49 | 54.0 |
| 50 | 77.8 |
| 51 | 84.0 |
| 52 | 43.7 |

As noted above, the invention compounds are potent modulators of chemokine receptor activity, and as such are useful medical agents for preventing and treating inflammatory disease and viral infections such as HIV. The compounds will typically be used in the form of pharmaceutical formulations. The following examples illustrate typical formulations.

Tablet Formulation

| Ingredient | Amount |
|---|---|
| Compound No. 2 | 150 mg |
| Corn Starch | 100 mg |
| Lactose | 140 mg |
| Magnesium Stearate (1%) | 10 mg |
| | 400 mg |

The above ingredients are blended to uniformity and pressed into a tablet. Such tablets are administered orally from one to four times a day for treatment of inflammation.

Preparation of Oral Suspension

| Ingredient | Amount |
|---|---|
| Compound No. 14 | 300 mg |
| Sorbitol Solution (70% N.F.) | 40 mL |
| Sodium Benzoate | 80 mg |
| Saccharin | 10 mg |
| Cherry Flavor | 50 mg |
| Distilled Water q.s. | 100 mL |

The sorbitol solution is added to 40 mL of distilled water and Compound No. 14 is suspended thereon. The saccharin, sodium benzoate, and flavor are added and dissolved. The volume is adjusted to 100 mL with distilled water. Each milliliter of syrup contains 3 mg of invention compound.

Example 7

Parenteral Solution

In a solution of 700 mL of propylene glycol and 200 mL of water for injection is suspended 20.0 g of Compound No. 17. The pH is adjusted to 5.5 with hydrochloric acid, and the volume is made up to 1000 mL with water. The formulation is sterilized, filled into 5.0 mL ampoules each containing 2.0 mL (40.0 mg of invention compound), and sealed under nitrogen.

Example 8

Combination Kit

A package kit having two compartments is prepared with nelfinavir in one compartment and a capsule formulation of Compound No. 23 in the second compartment. The combination of these agents is administered to patients infected with HIV.

The invention and the manner and process of making and using it are now described in such full, clear, concise, and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

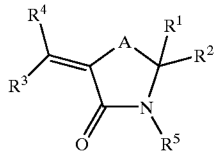

and pharmaceutically acceptable salts, esters, and amides thereof, wherein:

A is S;

$R^1$ and $R^2$ are independently hydrogen, halogen, hydroxy or lower alkoxy;

arylalkyl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl; or aryl or heteroaryl where each ring is substituted independently with up to three groups selected from halogen, hydroxy, carboxy, alkoxycarbonyl, cyano, trifluoromethyl, amino, mono- or dialkylamino, carbamoyl, carboxyalkyl, alkoxycarbonylalkyl, or sulfamoyl;

$R^3$ represents hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, sulfamoyl or sulfamoyl;

$R^4$ represents hydrogen, lower alkyl, cycloalkyl, aminoalkyl or mono- or dialkylaminoalkyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)$—$(CH_2)_n$—$XR^8R^9$;

X is N;

$R^6$ and $R^7$ independently represent hydrogen, lower alkyl, hydroxy, amino, or mono- or dialkylamino;

n is 0, 1, 2, 3 or4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

2. A compound of the formula

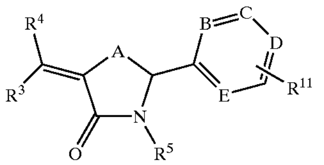

and pharmaceutically acceptable salts, esters, and amides thereof, wherein:

A is S;

$R^{11}$ is halogen, hydroxy, carboxy, alkoxycarbonyl, cyano, trifluoromethyl, amino, mono- or dialkylamino, carbamoyl, carboxyalkyl, alkoxycarbonylalkyl, or sulfamoyl;

$R^3$ represents hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^4$ represents hydrogen, lower alkyl, cycloalkyl, aminoalkyl or mono- or dialkylaminoalkyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)$—$(CH_2)_n$—$XR^8R^9$;

X is N;

$R^6$ and $R^7$ independently represent hydrogen, lower alkyl, hydroxy, amino, or mono- or dialkylamino;

n is 0, 1, 2, 3 or 4;

$R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group; and B, C, D and E independently represent CH or N, provided that no more than two of B, C, D and E are N.

3. A compound of the formula

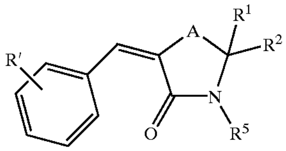

and pharmaceutically acceptable salts, esters, and amides thereof, wherein:

A is S;

$R^1$ and $R^2$ are independently hydrogen, lower alkyl, halogen, hydroxy or lower alkoxy; or aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

R' is carboxy, alkoxycarbonyl, cyano, trifluoromethyl, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)—(CH_2)_n—XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

4. A compound of the formula

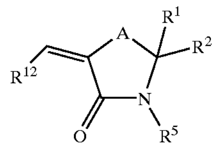

and pharmaceutically acceptable salts, esters, and amides thereof, wherein:

A is S;

$R^1$ and $R^2$ are independently hydrogen, halogen, hydroxy or lower alkoxy;

arylalkyl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl; or aryl or heteroaryl where each ring is substituted independently with up to three groups selected from halogen, hydroxy, carboxy, alkoxycarbonyl, cyano, trifluoromethyl, amino, mono- or dialkylamino, carbamoyl, carboxyalkyl, alkoxycarbonylalkyl, or sulfamoyl;

$R^{12}$ is cycloalkyl or heteroaryl optionally substituted with halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)—(CH_2)_n—XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

5. A compound of the formula

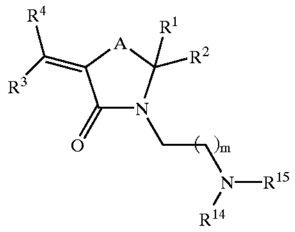

and pharmaceutically acceptable salts, esters, and amides thereof, wherein:

A is S;

$R^1$ and $R^2$ are independently hydrogen, halogen, hydroxy or lower alkoxy;

arylalkyl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl; or aryl or heteroaryl where each ring is substituted independently with up to three groups selected from halogen, hydroxy, carboxy, alkoxycarbonyl, cyano, trifluoromethyl, amino, mono- or dialkylamino, carbamoyl, carboxyalkyl, alkoxycarbonylalkyl, or sulfamoyl;

$R^3$ represents hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^4$ represents hydrogen, lower alkyl, cycloalkyl, aminoalkyl or mono- or dialkylaminoalkyl;

m is 0, 1, 2 or 3; and $R^{14}$ and $R^{15}$ independently represent hydrogen, lower alkyl, lower alkenyl or cycloalkyl; or $R^{14}$ and $R^{15}$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

6. A compound selected from the group consisting of:

5-(3-Fluorobenzylidene)-2-(3-fluorophenyl)-3-(3-morpholin-4-yl-propyl)-thiazolidin-4-one;

5-(3-Chlorobenzylidene)-2-(3-chlorophenyl)-3-(3-piperidin-1-yl-propyl)-thiazolidin-4-one;

5-Benzylidene-2-(3-chlorophenyl)-3-(3-piperidin-1-yl-propyl)-thiazolidin-4-one;

2-(3-Chlorophenyl)-5-(3-fluorobenzylidene)-3-(3-piperidin-1-yl-propyl)-thiazolidin-4-one;

3-(3-[1,4']Bipiperidinyl-1'-yl-propyl)-5-(3-fluorobenzylidene)-2-phenyl-thiazolidin-4-one;

3-(3-[1,4']Bipiperidinyl-1'-yl-propyl)-5-(3-fluorobenzylidene)-2-(3-fluorophenyl)-thiazolidin-4-one;

5-(3-Fluorobenzylidene)-3-(3-morpholin-4-yl-propyl)-2-phenyl-thiazolidin-4-one;

2-(3-Chlorophenyl)-3-(3-piperidin-1-yl-propyl)-5-(pyridin-4-yl-methylene)-thiazolidin-4-one;

2-(3-Chlorophenyl)-3-(3-piperidin-1-yl-propyl)-5-(1H-pyrrol-2-yl-methylene)-thiazolidin-4-one;

2-(3-Chlorophenyl)-3-(3-piperidin-1-yl-propyl)-5-(thiophen-3-yl-methylene)-thiazolidin-4-one;

2-(3-Chlorophenyl)-5-(1-methyl-1H-pyrrol-2-ylmethylene)-3-(3-piperidin-1-yl-propyl)-thiazolidin-4-one, and pharmaceutically acceptable salts, esters, and amides thereof.

7. A pharmaceutical composition comprising a compound according to any one of claims 1–6, 15, 16, or 27–34 in a mixture with a pharmaceutically acceptable excipient, diluent or carrier.

8. A pharmaceutical composition adapted for administration as an agent for treating AIDS comprising a therapeutically effective amount of a compound in admixture with a pharmaceutically acceptable excipient, diluent, or carrier, wherein said compound is of the formula

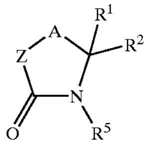

and pharmaceutically acceptable salts, esters, and amides thereof, wherein:

Z is —$CH_2$— or

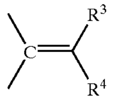

A is S, S═O or O═S═O;

$R^1$ and $R^2$ are independently hydrogen, lower alkyl, halogen, hydroxy or lower alkoxy; or aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^3$ and $R^4$ independently represent hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)$—$(CH_2)_n$—$XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

9. A method for modulation of a chemokine receptor activity in a mammal comprising administering an effective amount of a compound, such that chemokine receptor activity is mediated, wherein said compound is of the formula

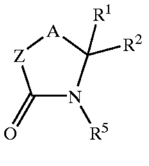

and pharmaceutically acceptable salts, esters, and amides thereof, wherein:

Z is —$CH_2$— or

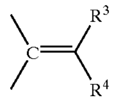

A is S, S═O or O═S═O;

$R^1$ and $R^2$ are independently hydrogen, lower alkyl, halogen, hydroxy or lower alkoxy; or aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^3$ and $R^4$ independently represent hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)$—$(CH_2)_n$—$XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

10. A method for modulation of the CCR-5 chemokine receptor activity in a mammal comprising administering an effect amount of a compound, such that CCR-5 chemokine receptor activity is modulated, wherein said compound is of the formula

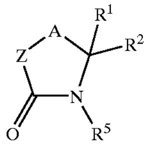

and pharmaceutically acceptable salts, esters, and amides thereof, wherein:

Z is —$CH_2$— or

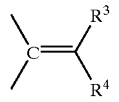

A is S, S═O or O═S═O;

$R^1$ and $R^2$ are independently hydrogen, lower alkyl, halogen, hydroxy or lower alkoxy; or aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^3$ and $R^4$ independently represent hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)$—$(CH_2)_n$—$XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

11. A method for preventing infection by HIV, treating infection by HIV, delaying the onset of AIDS, or treating AIDS comprising administering to a mammal in need of said treatment a therapeutically effective amount of a compound, wherein said compound is of the formula

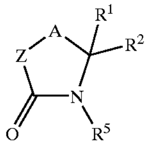

and pharmaceutically acceptable salts, esters, and amides thereof, wherein:

Z is —$CH_2$— or

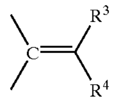

A is S, S=O or O=S=O;

$R^1$ and $R^2$ are independently hydrogen, lower alkyl, halogen, hydroxy or lower alkoxy; or aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^3$ and $R^4$ independently represent hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)—(CH_2)_n—XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

12. A compound of the formula

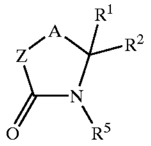

and pharmaceutically acceptable salts, esters, and amides thereof, wherein:

Z is —$CH_2$— or

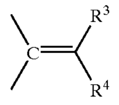

A is S=O or O=S=O;

$R^1$ and $R^2$ are independently hydrogen, lower alkyl, halogen, hydroxy or lower alkoxy; or aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^3$ and $R^4$ independently represent hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)—(CH_2)_n—XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

13. A compound of the formula

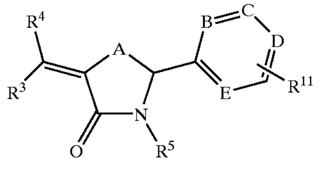

and pharmaceutically acceptable salts, esters, and amides thereof, wherein:

A is S=O or O=S=O;

$R^{11}$ is hydrogen, halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^3$ and $R^4$ independently represent hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)—(CH_2)_n—XR^8R^9$;

X is N;

$R^6$ and $R^7$ independently represent hydrogen, lower alkyl, hydroxy, amino, or mono- or dialkylamino;

n is 0, 1, 2, 3 or 4;

$R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group; and B, C, D and E independently represent CH or N, provided that no more than two of B, C, D and E are N.

14. A compound of claim 1, wherein $R^1$ is aryl, and substituted with halogen, lower alkyl, hydroxy, carboxy, alkoxycarbonyl, cyano, trifluoromethyl, amino, mono- or alkylamino, carbamoyl, carboxyalkyl, alkoxycarbonylalkyl, or sulfamoyl.

15. The compound of claim 3, wherein R' is halogen, lower alkyl, hydroxy, carboxy, alkoxycarbonyl, cyano, trifluoromethyl, amino, mono- or dialkylamino, carbamoyl, carboxyalkyl, alkoxycarbonylalkyl, or sulfamoyl.

16. The compound of claim 15, wherein R' is halogen.

17. The compound of claim 4, wherein $R^{12}$ is heteroaryl.

18. The compound of claim 5, wherein $R^3$ is heteroaryl.

19. The compound of claim 5, wherein $R^1$ is aryl or heteroaryl.

20. A compound, selected from the group consisting of:

2-(3-Chlorophenyl)-5-(2-ethylbutylidene)-3-(3-piperidin-1-yl-propyl)-thiazolidin-4-one;

2-(3-Chlorophenyl)-5-(3-dimethylamino-2,2-dimethylpropylidene)-3-(3-piperidin-1-yl-propyl)-thiazolidin-4-one;

2-(3-Chlorophenyl)-5-cyclohexylmethylene-3-(3-piperidin-1-yl-propyl)-thiazolidin-4-one;

2-(3-Chlorophenyl)-3-[3-(2-diethylaminoethylsulfanyl) propyl]-5-(3-fluorobenzylidene)-thiazolidin-4-one;

3-(1-Benzylpiperidin-4-yl)-2-(3-chlorophenyl)-thiazolidin-4-one;

2-(3-Chlorophenyl)-3-(3-piperidin-1-yl-propyl)-5-(pyridin-3-ylmethylene)-thiazolidin-4-one;

2-(3-Chlorophenyl)-3-(3-piperidin-1-yl-propyl)-5-(quinolin-3-ylmethylene)-thiazolidin-4-one;

3-(1-Benzylpiperidin-4-yl)-2-(3-chlorophenyl)-5-(3-fluorobenzylidene)-thiazolidin-4-one;

2-(3-Chlorophenyl)-5-(furan-2-ylmethylene)-3-(3-piperidin-1-yl-propyl)-thiazolidin-4-one;

3-(3-Azepan-1-ylpropyl)-5-benzylidene-2-phenyl-thiazolidin-4-one, and pharmaceutically acceptable salts, esters, and amides thereof.

21. A compound, selected from the group consisting of:

3-(3-[1,4']Bipiperidinyl-1'-yl-propyl)-2-(3-chlorophenyl)-5-(3-fluorobenzylidene)-thiazolidin-4-one;

2-(3-Chlorophenyl)-5-(3-fluorobenzylidene)-3-(3-morpholin-4-yl-propyl)-thiazolidin-4-one;

5-Benzylidene-2-(3-chlorophenyl)-1-oxo-3-(3-piperidin-1-yl-propyl)-thiazolidin-4-one;

5-(3-Fluoro-benzylidene)-3-(3-piperidin-1-yl-propyl)-2-(3-trifluoromethyl-phenyl)-thiazolidin-4-one;

5-(3-Fluoro-benzylidene)-2-(3-fluoro-phenyl)-3-[3-(4-pyridin-2-yl-piperazin-1-yl)-propyl]-thiazolidin-4-one;

3-[3-(4-Cyclohexyl-piperazin-1-yl)-propyl]-5-(3-fluoro-benzylidene)-2-(3-fluoro-phenyl)-thiazolidin-4-one;

2-(3-Chloro-phenyl)-5-(3-fluoro-benzylidene)-3-[3-(4-pyridin-2-yl-piperazin-1-yl)-propyl]-thiazolidin-4-one;

2-(3-Chloro-phenyl)-5-(3-fluoro-benzylidene)-3-(3-morpholin-4-yl-propyl)-thiazolidin-4-one;

2-(3-Chloro-phenyl)-5-(3-fluoro-benzylidene)-3-[3-(4-pyrimidin-2-yl-piperazin-1-yl)-propyl]-thiazolidin-4-one;

2-(3-Chloro-phenyl)-3-[3-(4-pyridin-2-yl-piperazin-1-yl)-propyl]-5-(3-trifluoromethyl-benzylidene)-thiazolidin-4-one, and pharmaceutically acceptable salts, esters, and amides thereof.

22. A compound selected from the group consisting of:

2-(3-Chloro-phenyl)-3-(3-piperidin-1-yl-propyl)-5-(3-trifluoromethyl-benzylidene)-thiazolidin-4-one;

2-(3-Chloro-phenyl)-3-[3-(4-pyrimidin-2-yl-piperazin-1-yl)-propyl]-5-(3-trifluoromethyl-benzylidene)-thiazolidin-4-one;

5-Benzylidene-3-[3-(4-pyridin-2-yl-piperazin-1-yl)-propyl]-2-(3-trifluoromethyl-phenyl)-thiazolidin-4-one;

5-Benzylidene-3-[3-(4-pyrimidin-2-yl-piperazin-1-yl)-propyl]-2-(3-trifluoromethyl-phenyl)-thiazolidin-4-one;

5-Benzylidene-2-(3-fluoro-phenyl)-3-[3-(4-pyridin-2-yl-piperazin-1-yl)-propyl]-thiazolidin-4-one;

5-Benzylidene-2-(3-fluoro-phenyl)-3-(3-piperidin-1-yl-propyl)-thiazolidin-4-one;

5-Benzylidene-3-(3-[1,4']bipiperidinyl-1'-yl-propyl)-2-(3-fluoro-phenyl)-thiazolidin-4-one;

5-Benzylidene-3-[3-(4-cyclohexyl-piperazin-1-yl)-propyl]-2-(3-fluoro-phenyl)-thiazolidin-4-one;

5-Benzylidene-2-(3-nitro-phenyl)-3-[3-(4-pyrimidin-2-yl-piperazin-1-yl)-propyl]-thiazolidin-4-one;

5-Benzylidene-2-(3-chloro-phenyl)-3-[3-(4-pyridin-2-yl-piperazin-1-yl)-propyl]-thiazolidin-4-one, and pharmaceutically acceptable salts, esters, and amides thereof.

23. A compound selected from the group consisting of:

5-Benzylidene-3-(3-[1,4']bipiperidinyl-1'-yl-propyl)-2-(3-chloro-phenyl)-thiazolidin-4-one;

5-Benzylidene-2-(3-chloro-phenyl)-3-(3-morpholin-4-yl-propyl)-thiazolidin-4-one;

5-Benzylidene-2-(3-chloro-phenyl)-3-[3-(4-pyrimidin-2-yl-piperazin-1-yl)-propyl]-thiazolidin-4-one;

5-Benzylidene-2-(3-chloro-phenyl)-3-[3-(4-cyclohexyl-piperazin-1-yl)-propyl]-thiazolidin-4-one;

5-(3-Chloro-benzylidene)-3-[3-(4-pyrimidin-2-yl-piperazin-1-yl)-propyl]-2-(3-trifluoromethyl-phenyl)-thiazolidin-4-one;

5-(3-Chloro-benzylidene)-3-[3-(4-cyclohexyl-piperazin-1-yl)-propyl]-2-(3-trifluoromethyl-phenyl)-thiazolidin-4-one;

5-(3-Chloro-benzylidene)-2-(3-fluoro-phenyl)-3-[3-(4-pyridin-2-yl-piperazin-1-yl)-propyl]-thiazolidin-4-one;

5-(3-Chloro-benzylidene)-2-(3-fluoro-phenyl)-3-[3-(4-pyrimidin-2-yl-piperazin-1-yl)-propyl]-thiazolidin-4-one;

5-(3-Chloro-benzylidene)-3-[3-(4-cyclohexyl-piperazin-1-yl)-propyl]-2-(3-fluoro-phenyl)-thiazolidin-4-one;

5-(3-Chloro-benzylidene)-2-(3-chloro-phenyl)-3-[3-(4-pyridin-2-yl-piperazin-1-yl)-propyl]-thiazolidin-4-one;

5-(3-Chloro-benzylidene)-2-(3-chloro-phenyl)-3-[3-(4-pyrimidin-2-yl-piperazin-1-yl)-propyl]-thiazolidin-4-one;

5-(3-Chloro-benzylidene)-2-(3-chloro-phenyl)-3-[3-(4-cyclohexyl-piperazin-1-yl)-propyl]-thiazolidin-4-one, and pharmaceutically acceptable salts, esters, and amides thereof.

24. A compound of the formula

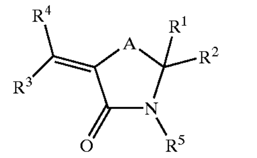

and pharmaceutically acceptable salts, esters, and amides thereof, wherein:

A is S;

$R^1$ is aryl, and substituted with halogen, lower alkyl, hydroxy, carboxy, alkoxycarbonyl, cyano, trifluoromethyl, amino, mono- or dialkylamino, carbamoyl, carboxyalkyl, alkoxycarbonylalkyl, or sulfamoyl;

$R^2$ is hydrogen, lower alkyl, halogen, hydroxy, lower alkoxy, aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^3$ represents hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, sulfamoyl or sulfamoyl;

$R^4$ represents hydrogen, lower alkyl, cycloalkyl, aminoalkyl or mono- or dialkylaminoalkyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)$—$(CH_2)_n$—$XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

25. A compound of the formula

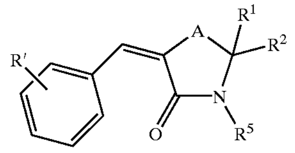

and pharmaceutically acceptable salts, esters, and amides thereof, wherein:

A is S═O or O═S═O;

$R^1$ and $R^2$ are independently hydrogen, lower alkyl, halogen, hydroxy or lower alkoxy; or aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

R' is hydrogen, halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)$—$(CH_2)_n$—$XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

26. A compound of the formula

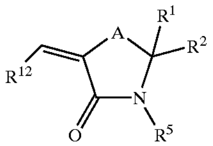

and pharmaceutically acceptable salts, esters, and amides thereof, wherein:

A is S═O or O═S═O;

$R^1$ and $R^2$ are independently hydrogen, lower alkyl, halogen, hydroxy or lower alkoxy; or aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^{12}$ is cycloalkyl or heteroaryl optionally substituted with halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^5$ represents a carbocyclic group containing from 3–7 members, up to two of which members are optionally hetero atoms selected from oxygen and nitrogen, where the carbocyclic group is optionally substituted with one or two groups selected from halogen, lower alkyl, lower alkoxy, mono- or dialkylamino, aryl, arylalkyl or a heterocyclic group; or $R^5$ is $(CR^6R^7)—(CH_2)_n—XR^8R^9$;

X is N;

$R^6$ and $R^7$ independently represent hydrogen, lower alkyl, hydroxy, amino, or mono- or dialkylamino;

n is 0, 1, 2, 3 or 4; and $R^8$ and $R^9$ independently represent hydrogen, lower alkyl, lower alkenyl, aminoalkyl, alkylaminoalkyl, dialkylaminoalkyl or cycloalkyl; or $R^8$ and $R^9$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

27. A compound of the formula

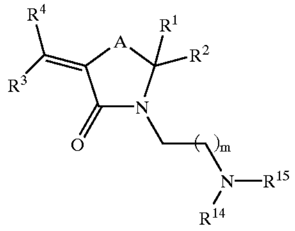

and pharmaceutically acceptable salts, esters, and amides thereof, wherein:

A is S═O or O═S═O;

$R^1$ and $R^2$ are independently hydrogen, lower alkyl, halogen, hydroxy or lower alkoxy; or aryl, arylalkyl, heteroaryl or heteroarylalkyl where each ring is optionally substituted independently with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^{3'}$ represents hydrogen, lower alkyl, cycloalkyl, aminoalkyl or mono- or dialkylaminoalkyl; or aryl or heteroaryl optionally substituted with up to three groups selected from halogen, lower alkyl, lower alkoxy, hydroxy, carboxy, alkoxycarbonyl, cyano, nitro, trifluoromethyl, amino, mono- or dialkylamino, carbamoyl, carboxyalkyl, alkoxycarbonylalkyl, or sulfamoyl;

$R^4$ represents hydrogen, lower alkyl, cycloalkyl, aminoalkyl or mono- or dialkylaminoalkyl;

m is 0, 1, 2 or 3; and $R^{14}$ and $R^{15}$ independently represent hydrogen, lower alkyl, lower alkenyl or cycloalkyl; or $R^{14}$ and $R^{15}$ together with the nitrogen to which they are attached form a heterocyclic ring containing from 5–7 members, up to two of which members are optionally hetero atoms selected from oxygen, sulfur and nitrogen, where the heterocyclic ring is optionally substituted with one or two groups selected from halogen, lower alkyl, lower alkoxy, mono- or dialkylamino, aryl, heteroaryl, arylalkyl, heteroarylalkyl, cycloalkyl or a heterocyclic group.

28. A pharmaceutical composition adapted for administration as an agent for treating HIV infection, comprising a therapeutically effective amount of a compound in admixture with a pharmaceutically acceptable excipient, diluent, or carrier, wherein said compound is a compound of any one of claims 1–6, 12, 13 or 20–27.

* * * * *